(12) United States Patent
Miyasato et al.

(10) Patent No.: US 12,004,844 B2
(45) Date of Patent: Jun. 11, 2024

(54) INFORMATION ACQUISITION APPARATUS AND SIGNAL PROCESSING METHOD

(71) Applicant: CANON KABUSHIKI KAISHA, Tokyo (JP)

(72) Inventors: Takuro Miyasato, Tokyo (JP); Kazuhiko Fukutani, Yokohama (JP); Ryuichi Nanaumi, Tokyo (JP); Kota Nakano, Tokyo (JP); Jumpei Shirono, Yokohama (JP); Kenji Mitsuhashi, Kawasaki (JP); Kazuhito Oka, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 889 days.

(21) Appl. No.: 16/285,749

(22) Filed: Feb. 26, 2019

(65) Prior Publication Data
US 2019/0183349 A1   Jun. 20, 2019

Related U.S. Application Data

(63) Continuation of application No. PCT/JP2017/029857, filed on Aug. 22, 2017.

(30) Foreign Application Priority Data

Aug. 30, 2016   (JP) .................. 2016-168205

(51) Int. Cl.
*A61B 5/00*   (2006.01)
*A61B 8/08*   (2006.01)
(Continued)

(52) U.S. Cl.
CPC .......... *A61B 5/0095* (2013.01); *A61B 5/4312* (2013.01); *A61B 8/13* (2013.01);
(Continued)

(58) Field of Classification Search
None
See application file for complete search history.

(56) References Cited

U.S. PATENT DOCUMENTS

| 5,713,356 | A | 2/1998 | Kruger |
| 7,916,283 | B2 | 3/2011 | Fukutani et al. |

(Continued)

FOREIGN PATENT DOCUMENTS

| JP | 2013-172810 | 9/2013 |
| JP | 2013-208422 | 10/2013 |

(Continued)

OTHER PUBLICATIONS

Oruganti, et al., "Vessel Filtering of Photoacoustic Images", Proc. SPIE, vol. 8581 (2013) 85811W-1 to 85811W-10.

*Primary Examiner* — Katherine L Fernandez
(74) *Attorney, Agent, or Firm* — VENABLE LLP

(57) ABSTRACT

Employed is an information acquisition apparatus which acquires characteristic information about an object using a reception signal of acoustic waves generated by the object that is irradiated with light, the apparatus having: region acquisition unit for acquiring information indicating a plurality of regions of mutually different characteristics, in the object; sound velocity determination unit for determining sound velocity in the plurality of regions, using the information indicating the plurality of regions; and characteristic information acquisition unit for acquiring the characteristic information about the object, using the sound velocity and the reception signal.

6 Claims, 17 Drawing Sheets

(51) Int. Cl.
*A61B 8/13* (2006.01)
*A61B 8/14* (2006.01)
*A61B 8/15* (2006.01)
*A61B 5/055* (2006.01)

(52) U.S. Cl.
CPC ............... *A61B 8/14* (2013.01); *A61B 8/15* (2013.01); *A61B 8/5261* (2013.01); *A61B 5/055* (2013.01); *A61B 5/4872* (2013.01); *A61B 5/489* (2013.01); *A61B 5/7425* (2013.01); *A61B 5/7485* (2013.01)

(56) References Cited

U.S. PATENT DOCUMENTS

| | | | |
|---|---|---|---|
| 8,260,403 B2 | 9/2012 | Fukutani et al. | |
| 8,300,224 B2 | 10/2012 | Nakajima et al. | |
| 8,396,534 B2 | 3/2013 | Fukutani et al. | |
| 8,654,613 B2 | 2/2014 | Fukutani | |
| 8,687,868 B2 | 4/2014 | Fukutani et al. | |
| 8,864,667 B2 | 10/2014 | Asao et al. | |
| 8,942,058 B2 | 1/2015 | Fukutani | |
| 9,131,851 B2 | 9/2015 | Fukutani et al. | |
| 9,247,923 B2 | 2/2016 | Baba et al. | |
| 9,523,659 B2 | 12/2016 | Mitsuhashi | |
| 9,560,973 B2 | 2/2017 | Fukutani | |
| 9,566,006 B2 | 2/2017 | Nanaumi | |
| 9,572,531 B2 | 2/2017 | Fukutani | |
| 9,615,751 B2 | 4/2017 | Fukutani | |
| 9,737,216 B2 | 8/2017 | Nanaumi | |
| 9,782,080 B2 | 10/2017 | Suita et al. | |
| 9,883,807 B2 | 2/2018 | Fukutani | |
| 10,064,557 B2 | 9/2018 | Nanaumi et al. | |
| 10,165,948 B2 | 1/2019 | Nagae et al. | |
| 2010/0087733 A1 | 4/2010 | Nakajima et al. | |
| 2010/0191109 A1 | 7/2010 | Fukutani et al. | |
| 2012/0095337 A1* | 4/2012 | Alexandru | G01S 15/8915 600/442 |
| 2012/0130222 A1 | 5/2012 | Kobayashi et al. | |
| 2012/0296192 A1 | 11/2012 | Fukutani et al. | |
| 2013/0085371 A1 | 4/2013 | Miyasato | |
| 2014/0036636 A1 | 2/2014 | Miyasato | |
| 2014/0058245 A1 | 2/2014 | Oishi et al. | |
| 2014/0066744 A1 | 3/2014 | Fukutani | |
| 2014/0296690 A1 | 10/2014 | Miyasato et al. | |
| 2014/0303473 A1 | 10/2014 | Nanaumi | |
| 2014/0360271 A1 | 12/2014 | Fukutani | |
| 2016/0174849 A1 | 6/2016 | Nanaumi et al. | |
| 2016/0184133 A1 | 6/2016 | Miyasato et al. | |
| 2016/0270667 A1 | 9/2016 | Nakajima et al. | |
| 2017/0032519 A1* | 2/2017 | Thornton | G06T 7/11 |
| 2017/0065180 A1 | 3/2017 | Miyasato et al. | |
| 2017/0065181 A1 | 3/2017 | Masaki et al. | |
| 2017/0065252 A1 | 3/2017 | Suehira et al. | |
| 2017/0119253 A1 | 5/2017 | Suehira et al. | |
| 2017/0156601 A1 | 6/2017 | Sudo et al. | |
| 2017/0172419 A1 | 6/2017 | Oishi et al. | |
| 2017/0215739 A1 | 8/2017 | Miyasato | |
| 2017/0215804 A1 | 8/2017 | Miyasato | |
| 2017/0238862 A1 | 8/2017 | Fukutani et al. | |
| 2017/0265750 A1 | 9/2017 | Iizuka et al. | |
| 2017/0273568 A1 | 9/2017 | Miyasato | |
| 2017/0311810 A1* | 11/2017 | Nakamura | A61B 5/4312 |
| 2017/0311927 A1 | 11/2017 | Yao et al. | |
| 2017/0325693 A1 | 11/2017 | Fukui et al. | |
| 2018/0177405 A1* | 6/2018 | Sasaguri | A61B 5/14535 |
| 2018/0192882 A1 | 7/2018 | Baba et al. | |
| 2018/0368696 A1 | 12/2018 | Abe et al. | |
| 2018/0368697 A1 | 12/2018 | Fukutani et al. | |
| 2019/0307334 A1* | 10/2019 | Wang | A61B 5/024 |

FOREIGN PATENT DOCUMENTS

| | | |
|---|---|---|
| JP | 2014-147825 | 8/2014 |
| JP | 2016-087220 | 5/2016 |
| WO | WO 2016/072525 * | 5/2016 |

* cited by examiner

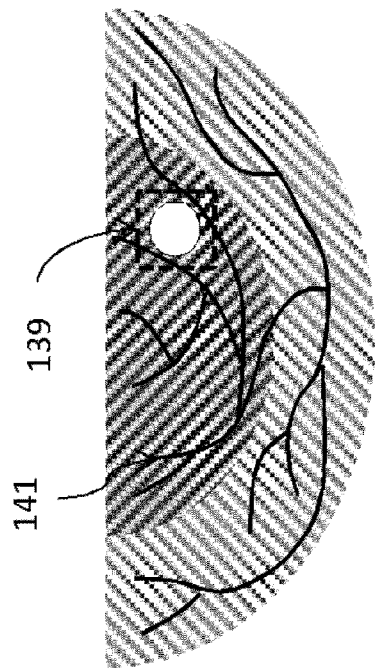
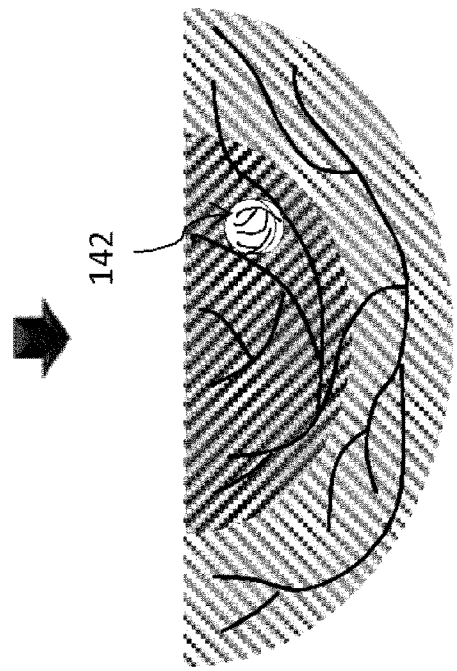
FIG. 6C
FIG. 6D
FIG. 6A
FIG. 6B

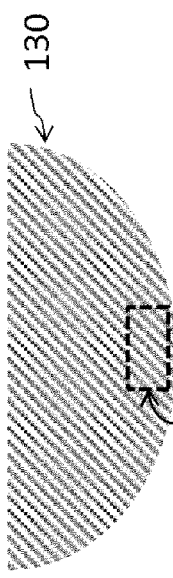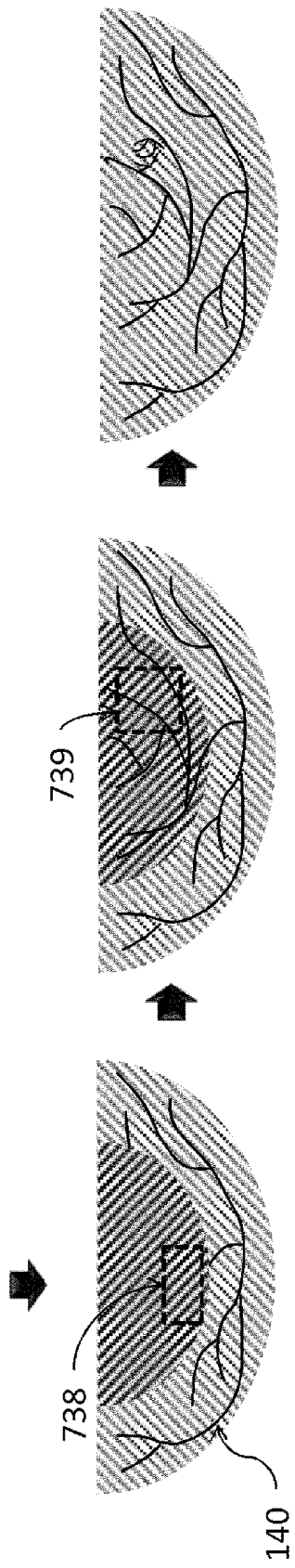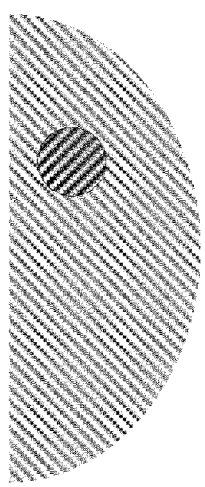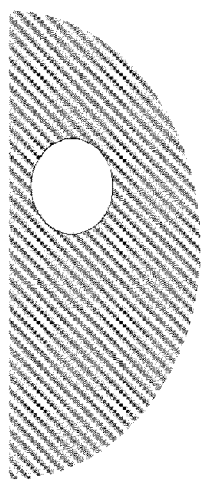

INFORMATION ACQUISITION APPARATUS AND SIGNAL PROCESSING METHOD

CROSS-REFERENCE TO RELATED APPLICATIONS

This application is a Continuation of International Patent Application No. PCT/JP2017/029857, filed on Aug. 22, 2017, which claims the benefit of Japanese Patent Application No. 2016-168205, filed on Aug. 30, 2016, both of which are hereby incorporated by reference herein in their entirety.

BACKGROUND OF THE INVENTION

Field of the Invention

The present invention relates to an information acquisition apparatus and to a signal processing method.

Background Art

Active research is being pursued, centered on the medical field, concerning apparatus that causes pulsed light, which is irradiated onto the object from a light source such as a laser, to propagate within the object, and that obtains information about the interior of the object. Patent Literature 1 proposes photoacoustic tomography (hereafter referred to as PAT) as one such technique for acquisition of object information using pulsed light.

Photoacoustic tomography involves irradiating an object with pulsed light, receiving, at a plurality of positions, acoustic waves generated by a light-absorbing body in the interior of the object, and calculating a characteristic distribution related to light absorption, for instance through calculation of a reception signal on the basis of Expression (1).

[Math. 1]

$$p_0(r_0) = \frac{\sum_{i}^{N} b\left(r_i, t = \frac{|r_i - r_0|}{c(r_i, r_0)}\right) \cdot \Delta\Omega_i}{\sum_{i}^{N} \Delta\Omega_i} \quad (1)$$

$$b(r, t) = 2p(r, t) - 2t\frac{\partial p(r, t)}{\partial t}$$

In the expression, $r_0$ represents a position vector denoting an imaging position, $p_0(r_0)$ represents initial sound pressure at the imaging position, and $r_i$ represents the position of an i-th element. Further, $\Delta\Omega_i$ rents the solid angle envisaged for the i-th element, from the imaging position, and N denotes the number of elements used for imaging. Expression (1) denotes in-phase addition (back projection) as a result of for instance a process of differentiating a reception signal $p(r_i, t)$, with solid angle weighting of the result. Further, $c(r_i, r_0)$ denotes the average sound velocity of a straight line joining the i-th element and the imaging position $r_0$. The variable t in Expression (1) is the time (propagation time) of propagation of photoacoustic waves in a sound ray that joins the imaging position $r_0$ and the i-th element $r_i$.

CITATION LIST

Patent Literature

PTL 1: U.S. Pat. No. 5,713,356

Non Patent Literature

NPL 1: T. Oruganti, J. G. Laufer, B. E. Treeby, "Vessel filtering of photoacoustic images" and Proc. SPIE 8581 (2013) 85811W.

In tomography using acoustic waves, as described above, propagation of the acoustic waves in order to reconstruct a given voxel takes some time. It is found that a sound velocity distribution between elements and voxels is required to that end. Specifically, a sound velocity distribution of the interior of the object is necessary for the purpose of performing accurate reconstruction on the basis of acquired signals. It is however difficult to acquire an unknown sound velocity distribution of the interior of the object with good precision.

The present invention was arrived at in the light of the above problems. It is a goal of the present invention to acquire, with good precision, information pertaining to a sound velocity distribution of the interior of an object.

SUMMARY OF THE INVENTION

The present invention employs the configuration below. Specifically, the present invention is an information acquisition apparatus which acquires characteristic information about an object using a reception signal of acoustic waves generated by the object that is irradiated with light, the apparatus comprising:
region acquisition unit configured to acquire information indicating a plurality of regions of mutually different characteristics, in the object;
sound velocity determination unit configured to determine sound velocity in the plurality of regions using the information indicating the plurality of regions; and
characteristic information acquisition unit configured to acquire the characteristic information about the object, using the sound velocity and the reception signal.

Further, the present invention employs the configuration below. Specifically, the present invention is also a signal processing method for acquiring characteristic information about an object using a reception signal of acoustic waves generated by the object that is irradiated with light, the method comprising:
a region acquisition step of acquiring information indicating a plurality of regions of mutually different characteristics, in the object;
a sound velocity determination step of determining sound velocity in the plurality of regions, using the information indicating the plurality of regions; and
a characteristic information acquisition step of acquiring the characteristic information about the object, using the sound velocity and the reception signal.

Further features of the present invention will become apparent from the following description of exemplary embodiments with reference to the attached drawings.

BRIEF DESCRIPTION OF THE DRAWINGS

FIGS. 6A to 6D are explanatory diagrams of sound velocity determination method.

FIGS. 17A to 17G is a concrete example of flow in Embodiment 5.

DESCRIPTION OF THE EMBODIMENTS

Figure 1:
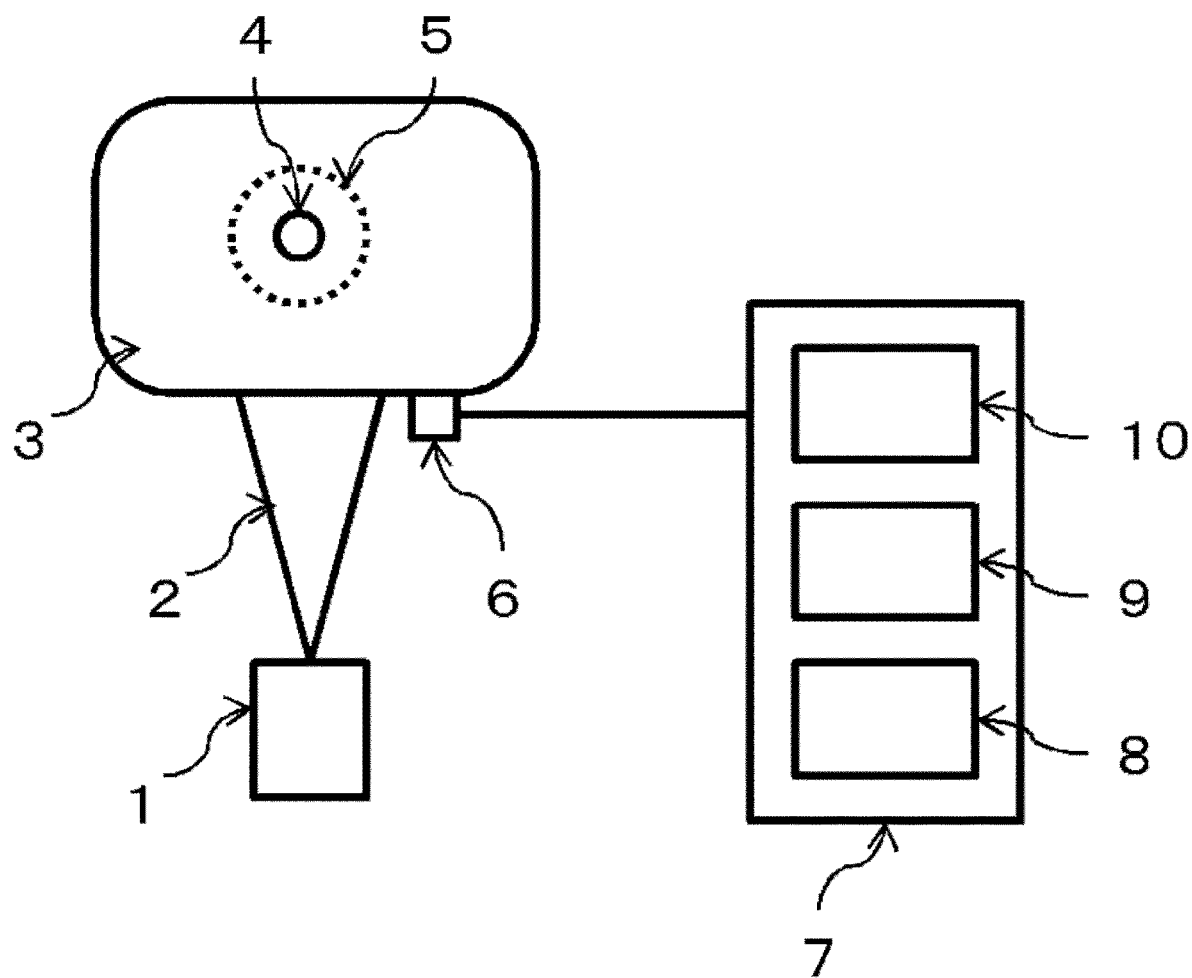
FIG. 1 is an apparatus diagram for explaining an embodiment of the present invention.

Preferred embodiments of the present invention will be explained next with reference to accompanying drawings. The dimensions, materials, shapes and relative arrangement of the constituent components described below are to be modified as appropriate depending on the configuration and attendant conditions of the apparatus where the invention is to be adopted. Accordingly, the scope of the invention is not meant to be limited to the disclosure that follows below.

The present invention relates to a technique for detecting acoustic waves propagating from an object, and generating and acquiring characteristic information about the interior of the object. Accordingly, the present invention can be grasped as an object information acquisition apparatus or control method thereof, an object information acquisition method, a signal processing method, an information processing apparatus, or an information processing method. The present invention can also be grasped as a program for causing an information processing apparatus provided with hardware resources such as a CPU and a memory, to execute the foregoing methods, and as a storage medium in which such a program is stored. The storage medium may be a computer-readable non-transitory storage medium.

The information acquisition apparatus includes a photoacoustic imaging apparatus that uses a photoacoustic effect, the photoacoustic imaging apparatus irradiating light (electromagnetic waves) onto an object to receive acoustic waves generated as a result in the object, and acquiring, in the form of image data, characteristic information about the object. Herein the term characteristic information indicates information about a characteristic value generated using a reception signal obtained through reception of photoacoustic waves, and that corresponds to respective positions inside the object.

The characteristic information acquired by the photoacoustic apparatus is a value that reflects an absorption rate of light energy. For instance, characteristic information may include a generation source of acoustic waves generated through irradiation of light of a single wavelength, initial sound pressure within the object, or light energy absorption density or an absorption coefficient derived from the initial sound pressure. The concentration of substances that make up tissue can be acquired on the basis of characteristic information obtained from a plurality of mutually different wavelengths. An oxygen saturation distribution can be calculated by working out an oxygenated hemoglobin concentration and a deoxygenated hemoglobin concentration, as the substance concentration. For instance, glucose concentration, collagen concentration, melanin concentration, or a volume fraction of fats or water can be worked out herein as the substance concentration.

A two-dimensional or three-dimensional characteristic information distribution is obtained on the basis of characteristic information at each position within the object. The distribution data can be generated as image data. The characteristic information may be worked out not as numerical value data but, instead, as distribution information at each position within the object. Specifically, characteristic information is distribution information such as an initial sound pressure distribution, an energy absorption density distribution, an absorption coefficient distribution or an oxygen saturation distribution.

The term acoustic waves in the present invention indicates typically ultrasonic waves, and includes elastic waves referred to as sound waves or acoustic waves. Electrical signals obtained through conversion of acoustic waves by means of a transducer or the like are also referred to as acoustic signals. However, the terms ultrasonic waves or acoustic waves in the present specification are not meant to limit the wavelengths of these elastic waves. Acoustic waves generated on account of the photoacoustic effect will also be called photoacoustic waves or photoultrasonic waves. Electrical signals derived from photoacoustic waves will also be called photoacoustic signals.

In the embodiments below, a photoacoustic apparatus that irradiates pulsed light onto an object, receives acoustic waves from the object derived from a photoacoustic effect, and analyzes the acoustic waves to thereby acquire a distribution of a light-absorbing body within the object, is used as the information acquisition apparatus. A breast of a subject is conceivable herein as the object. However, the object is not limited thereto, and may conceivably be a site of the subject, or a non-human object such as an animal, an inanimate object or a phantom.

Apparatus Configuration

FIG. 1 is a schematic diagram of a photoacoustic apparatus according to the present embodiment. The photoacoustic apparatus in the present embodiment has a light irradiation unit 1 that projects pulsed light 2 onto an object, an acoustic wave reception unit 6, and an information processing unit 7. The information processing unit 7 has a region segmentation unit 8, a sound velocity determining unit 9, and characteristic information acquisition unit 10. The measurement target is an object 3, in the interior of which there is present an absorbing body 4 that absorbs the pulsed light 2 and generates thereupon acoustic waves 5.

The light irradiation unit 1 is made up of a light source that emits pulsed light and an irradiation optical system that irradiates the generated pulsed light onto the object 3. The pulsed light 2 diffuses within the object (living tissue in a case where object is a living body) and is absorbed by the absorbing body 4. The acoustic waves 5 generated as a result propagate within the object, and are detected by the acoustic wave reception unit 6. The acoustic wave reception unit 6 converts the acoustic waves 5 to an analog electrical signal. The analog electrical signal is subjected to amplification processing and digital conversion processing, and is stored in a memory (not shown) as reception data. The information processing unit 7, which has the region segmentation unit 8, the sound velocity determining unit 9 and the characteristic information acquisition unit 10, calculates characteristic information about the interior of the object on the basis of region segmentation information about the interior of the object, sound velocity at respective regions, and reception data.

The detailed materials, structures and functions of the various constituent elements will be explained next.

Light Irradiation Unit

The light irradiation unit has a light source that emits light and an optical system that guides the light outputted by the light source towards the object. The light includes pulsed light, for instance a so-called square wave or triangular wave.

The pulse width of the light outputted by the light source may be of at least 1 ns and not more than 100 ns. The wavelength of the light may lie in the range of about 400 nm to 1600 nm. In a case where blood vessels are to be imaged at high resolution there may be used a wavelength (at least 400 nm and no more than 700 nm) at which absorption by blood vessels is significant. In a case where a deep site of a living body is to be imaged, there may be typically used light of a wavelength (at least 700 nm and no more than 1100 nm) with little absorption in background tissue (for instance water and fat) of the living body.

A laser or a light-emitting diode can be used as the light source. The light source may be of modifiable wavelength in measurements utilizing light of a plurality of wavelengths. In a case where the object is to be irradiated with a plurality of wavelengths, there can be prepared a plurality of light sources that generate light of mutually different wavelengths, such that respective beams are irradiated alternately from the light sources. In a case where a plurality of light sources is used, the foregoing will be referred to collectively hereafter as light source. Various types of laser, such as a solid laser, a gas laser, a dye laser or a semiconductor laser, can be used as the laser. For instance, a pulsed laser such as a Nd:YAG laser or an alexandrite laser may be used as the light source. Herein a Ti:sapphire laser or an OPO (Optical Parametric Oscillators) laser having an Nd:YAG laser as pumping light may be used as the light source. A flash lamp or a light-emitting diode may also be used as the light source 111. A microwave source may also be used as the light source 111.

Optical elements such as lenses, mirrors, prisms, optical fibers, diffusion plates, shutters and the like can be used in the optical system.

The allowable intensity of light irradiated onto living tissue is prescribed by a maximum permissible exposure (MPE) pursuant to the safety standards below (For instance IEC 60825-1: Safety of laser products; JIS C 6802: Safety of laser products; FDA: 21CFR Part 1040.10; ANSI Z136.1: Laser Safety Standards). The maximum permissible exposure restricts the intensity of light that can be irradiated per unit surface area. Accordingly, a greater light quantity can be guided to an object E by irradiating light all at once onto a large surface area of the object E. Photoacoustic waves can be received therefore at a high SN ratio. In a case where the object is living tissue such as a breast, an output unit of optical system may be configured including for instance a diffusion plate for diffusing light, in order to irradiate a high-energy light beam of a wider diameter. In a photoacoustic microscope, by contrast, the light output unit of the optical system may be configured using a lens or the like, such that beams are projected while focused, with a view to increasing resolution. The light irradiation unit may be provided with a scanning mechanism for mechanically moving the optical system, and may be provided with a plurality of light outlets that can be selected by a switch.

The light irradiation unit may lack an optical system, and light from the light source be thus irradiated directly onto the object.

Acoustic Wave Reception Unit

The acoustic wave reception unit has a receiver that receives a signal physically, and a signal processing unit. The receiver detects photoacoustic waves generated on the surface of the object and in the interior of the object, and converts the detected waves to an analog electrical signal. For instance, a transducer using piezoelectric phenomena, a transducer using light resonance or a transducer using changes in capacitance can be used herein as the receiver. To detect acoustic waves at a plurality of positions, a plurality of acoustic wave detection elements may be arrayed in one, two or three dimensions, and may be configured to be mechanically scannable by a scanning mechanism of an acoustic wave detection unit. The elements may be a single element, with focusing by an acoustic lens, such that the position of an acoustic wave generation source can be specified. The element corresponds to the conversion unit of the present invention. A probe having the acoustic wave reception unit may be provided with a grip that enables a user to grip the probe. Specifically, the probe according to the present embodiment may be a handheld probe.

The signal processing unit amplifies the analog electrical signal and subjects the resulting signal to digital conversion. The signal processing unit is made up of for instance an amplifier, an A/D converter, and an FPGA (Field Programmable Gate Array) chip. The acoustic wave reception unit is provided with a plurality of elements; in a case where a plurality of reception signals is obtained, it is preferable that the plurality of signals can be processed simultaneously in order to shorten processing time. Reception signals received at a same position with respect to an object may be integrated in order to raise the SN ratio. The integration method resorted to herein may be simple addition, or also addition averaging, and weighted addition. The term "reception signal" in the present specification encompasses conceptually both analog signals outputted by an acoustic wave detector or a photodetector, as well as digital signals resulting from subsequent AD conversion.

Information Processing Unit

The information processing unit 7 has the region segmentation unit 8, the sound velocity determining unit 9 and the characteristic information acquisition unit 10. As the information processing unit 7 there can be used an information processing apparatus such as a PC or workstation provided with for instance a CPU, a storage apparatus and a communication apparatus, and which runs according to instructions from a program deployed in a memory. A plurality of information processing apparatus working together may function as the information processing unit 7. Each functional block may be regarded as a program module that prompts execution of processing using the computational resources of the information processing apparatus. An information processing unit 7 not including structures such as the light irradiation unit 1 or the acoustic wave reception unit 6 may be provided by the user.

The computing unit of the information processing unit 7 can be configured out of a processor such as a CPU or GPU (Graphics Processing Unit), or an arithmetic circuit such as an FPGA (Field Programmable Gate Array) chip. These units may be made up of not just a single processor or a single arithmetic circuit, but also out of a plurality of processors and arithmetic circuits.

The storage unit of the information processing unit 7 can be configured in the form of a non-transitory storage medium such as a ROM (Read-Only Memory), a magnetic disk or a flash memory. The storage unit may be a volatile medium such as a RAM (Random Access Memory). The storage medium having a program stored thereon is a non-transitory storage medium. The storage unit may not only have just one storage medium, but may also be made up of a plurality of storage media.

The control unit of the information processing unit 7 is made up of an arithmetic element such as a CPU. The control unit controls the operation of the various structures of the photoacoustic apparatus. The control unit may control the various structures of the photoacoustic apparatus by receiving an instruction signal derived from various operations, such as initiation of measurements, from an input unit. The control unit reads a program code stored in the storage unit, and controls the operation of the various structures of the photoacoustic apparatus. For instance, the control unit may control an emission timing of the light source via a control line. In a case where the optical system includes a shutter, the control unit may control opening and closing of the shutter via a control line.

The information processing apparatus may double as a display control unit that controls display of image data on a display apparatus, not shown. The display apparatus may be an arbitrary display apparatus, for instance a liquid crystal display or a plasma display. A user interface (for instance mouse, keyboard or touch panel) of the information processing apparatus can be used as the below-described input unit. Different contrast/colors for each segmented region may be used in the display apparatus.

Region Segmentation Unit

The region segmentation unit segments regions in the interior of the object in accordance with distribution data that is obtained with a modality different from that of the photoacoustic apparatus, for instance an MRI image, a contrast MRI image, a reflection ultrasonic image or a transmission ultrasonic image, human body atlas data, or input data. The region segmentation unit acquires information indicating a plurality of segmented regions. Specifically, the region segmentation unit acquires information indicating a boundary between the segmented regions. Any method may be resorted to herein, so long as regions inside the object can be segmented on the basis of specific differences, for instance tissue differences, of the interior of the object and that are expected to be accompanied with changes in sound velocity. The region segmentation unit corresponds to the region acquisition unit of the present invention.

Examples of segmentation methods include a method that involves dividing distribution data obtained with a modality into a region in which intensity is equal to or higher than a given threshold value, and a region in which intensity is lower than the threshold value. Other examples of segmentation methods include segmentation at boundaries between tissues in human body atlas data. In yet another example, a method involves dividing distribution data obtained by the photoacoustic apparatus into a region where an absorbing body is reflected significantly and into a region in which the absorbing body is virtually not reflected. In a further exemplary method, a user such as a doctor or a technician designates a boundary using an input unit. The distribution data obtained with a given modality and distribution data of a human body atlas may differ in shape with respect to distribution data obtained by the photoacoustic apparatus, depending for instance on the measurement position. Therefore, distribution data obtained with a given modality and distribution data of a human body atlas may be deformed/aligned beforehand, prior to region segmentation, to the shape of the object at the time of measurement using photoacoustic waves.

Sound Velocity Determining Unit

The sound velocity determining unit determines sound velocity at regions resulting from segmentation by the region segmentation unit. The sound velocity determining unit acquires information indicating sound velocity (sound velocity distribution) at the plurality of determined regions. An example of the determination method will be explained next. Firstly, a region of interest ROI is set (designated) within the object, for instance by means of an input unit. A plurality of sound velocity values in the segmented regions is set within a range expected for the segmented regions, and an image of the region of interest is reconstructed using the sound velocity values. The user selects an optimal sound velocity value through comparison of images corresponding to the sound velocity values, and designates the sound velocity using the input unit. An appropriate value can be determined thus through setting of a sound velocity value to within a range of possible values of sound velocity, and through reception of an input while the sound velocity value is updated. The sound velocity determining unit corresponds to the sound velocity determination unit of the present invention.

Another determination method may involve designating an objective function, and determining a sound velocity such that a value of the objective function, worked out on the basis of a distribution of the region of interest, takes on a maximum value. An appropriate value can be determined thus through setting of a sound velocity value to within a range of possible values of sound velocity, and through maximization of an objective function while the function is updated. The objective function is preferably a function such that a value thereof at a time where an observation target (for instance a blood vessel) can be observed with good precision is a maximum value. The objective function may include terms having, as indices, point resemblance/line resemblance/plane resemblance, and may include terms for boundary detection. Further, the objective function may include a constraint term so as to preclude clearly abnormal solutions. For instance, the indices described in NPL 1 can be used as indices of point resemblance/line resemblance/plane resemblance. As concrete examples of terms for boundary detection there can be used a total of differential values, in each direction, of a distribution of the region of interest.

There is no need for determining sound velocity in all the segmented regions at once, and a method may be resorted to wherein a respective sound velocity at each segmented region is determined sequentially. A preferred procedure in this case involves setting a region of interest at a region of the object close to an acoustic wave detection element, and determining the sound velocity at that region, and thereafter, setting a region of interest to a region close to the acoustic wave detection element, and determining sound velocity at that region. In a case where sound velocity is determined thus sequentially, it is preferable to determine sound velocity at a region close to the surface of the object, and thereafter, estimating sound velocity at a small region at a deeper position (i.e. more distant from the element). When determining thus sound velocity sequentially from the surface side (side close to the element), the precision of estimation of a deep site of the object is improved, since sound velocity at a shallow site traversed by a sound ray is known herein.

In a case where sound velocity is determined sequentially the objective function may be modified depending on the segmented region. Depending on the segmented region, the sound velocity can be modified within a range expected for that segmented region, and there may be displayed an image of the region of interest corresponding to each sound velocity. Otherwise, any sound velocity determination method may be resorted to, so long as the method yields an improved final image. To maximize (or minimize) an objective function, an initial value of sound velocity is set to an appropriate value; calculation precision can be improved or the calculation time shortened thereby. For instance, a typical sound velocity value for a living body or a sound velocity value of a medium present between the probe and the object is used herein as the initial value of sound velocity. The initial value is preferably prescribed in accordance with the temperature of the object, in view of the temperature dependence of sound velocity values. The range over which the sound velocity value may vary during maximization (or minimization) of the objective function may be limited to the vicinity of a sound velocity value determined depending on the type of the object tissue and on the object temperature.

Herein the term maximization encompasses not only an instance where the object function takes on a maximum value, but also an instance where the objective function is equal to or greater than a predetermined threshold value. Further, the term minimization encompasses not only an instance where the object function takes on a minimum value, but also an instance where the objective function is equal to or smaller than a predetermined threshold value. An instance where the objective function is largest or smallest, among calculation results over a predetermined number of times with updating of the sound velocity for a predetermined number of times, may be determined to be a maximized or minimized objective function, respectively.

Characteristic Information Acquisition Unit

The characteristic information acquisition unit calculates a distribution of the absorbing body in the interior of the object, using a reception signal, on the basis of region segmentation information about the object as calculated by the region segmentation unit, and sound velocity at each segmented region as calculated by the sound velocity determining unit. As the distribution calculation method there can be used for instance time-domain universal back projection, frequency-domain universal back projection, delay-and-sum, model-based reconstruction or time reversal. Not only an initial sound pressure distribution but also for instance an absorption coefficient distribution or substance concentration distribution according to a light quantity distribution can be created herein as the distribution information. The characteristic information acquisition unit corresponds to the characteristic information acquisition unit of the present invention.

Processing Procedure

Figure 2:
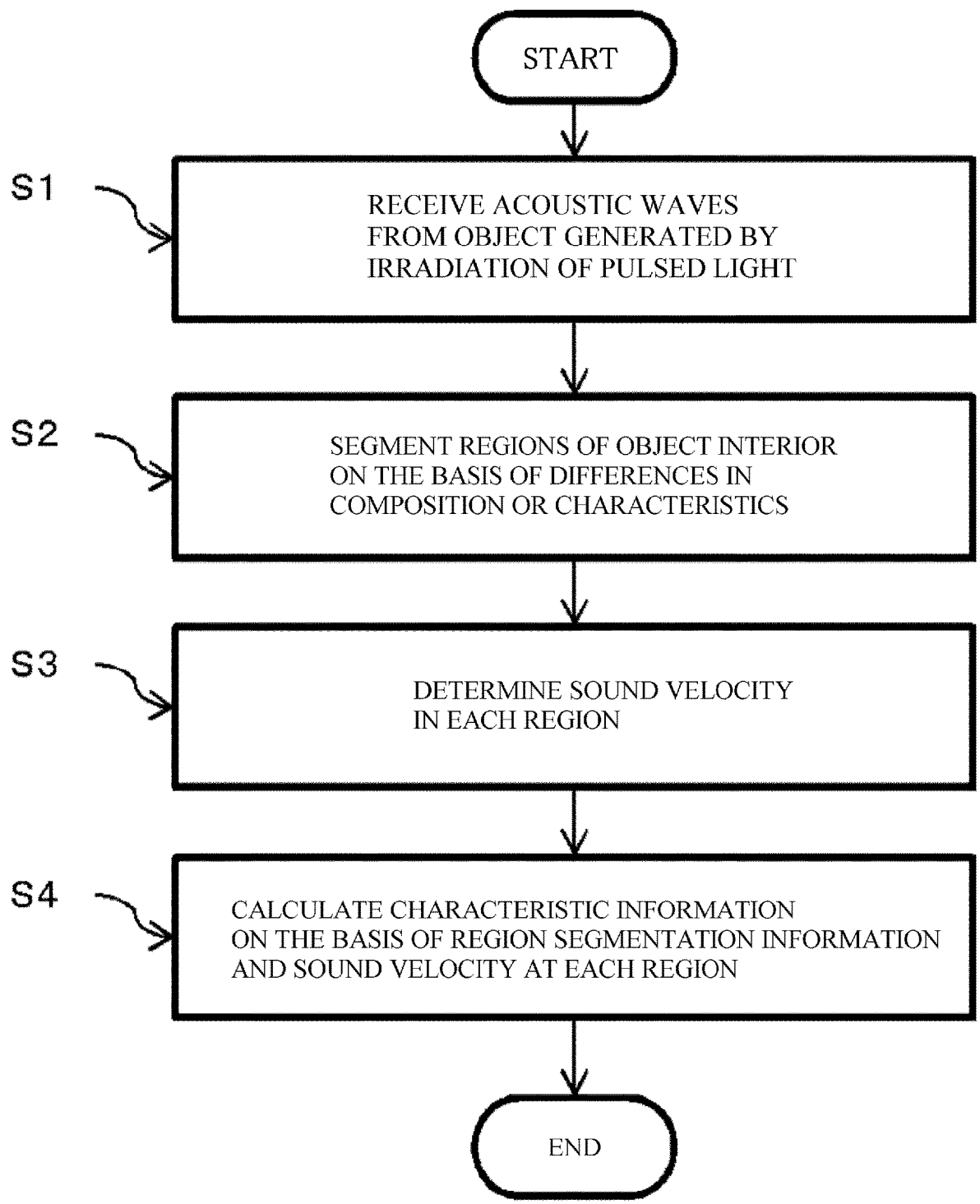
FIG. 2 is a flowchart for explaining an embodiment of the present invention.

An information acquisition method according to the present embodiment will be explained next with reference to the flowchart in FIG. 2.

(Step S1): pulsed light 2 is irradiated from the light irradiation unit 1 onto the object 3. Pulsed light propagating in the interior of the object is absorbed by the absorbing body 4 inside the object, whereupon acoustic waves 5 are generated on account of the photoacoustic effect. The acoustic wave reception unit 6 receives this acoustic wave and converts the acoustic wave to a reception signal.

(Step S2): the region segmentation unit 8 segments the interior of the object 3 into a plurality of regions where sound velocity can conceivably exhibit significant differences, on the basis of distribution information in which differences in composition and characteristics are known.

(Step S3): The sound velocity determining unit 9 determines sound velocity in each segmented region. Input information from an input unit, or an objective function, can be used for that determination. In a case where an objective function is used, there is set a plurality of sound velocity values, of each segmented region, within expected ranges, a respective reception signal is reconstructed for each set sound velocity value, to thereby acquire distribution information, and a sound velocity value is selected such that an objective function value is maximized.

(Step S4): the characteristic information acquisition unit 10 performs reconstruction by adjusting a delay time of the reception signal at each element and at each voxel, using the information about region segmentation, obtained in S2, and sound velocity at each segmented region obtained in S3. As a result, a substance concentration distribution is calculated in which there is used an initial sound pressure distribution, an absorption coefficient distribution and also spectroscopic information. Herein an imaging unit region at the time of reconstruction is referred to as a voxel in three-dimensional imaging and as a pixel in two-dimensional imaging.

For the purpose of acquiring sound velocity in a segmented region it is not necessary to acquire characteristic information, i.e. step S4 need not be executed in that case.

Further, step S1 may be not executed by the information acquisition apparatus, in which case another apparatus different from the information acquisition apparatus receives the acoustic waves. Herein the information acquisition apparatus can execute signal processing by acquiring a signal resulting from conversion of the acoustic waves at the other apparatus.

Embodiment 1

In the present embodiment, a PAT diagnosis apparatus will be described in which a human breast is measured by way of a bowl-shaped probe, to acquire blood information and a blood oxygen saturation distribution of the interior of the breast.

Configuration and Operation

Figure 3:
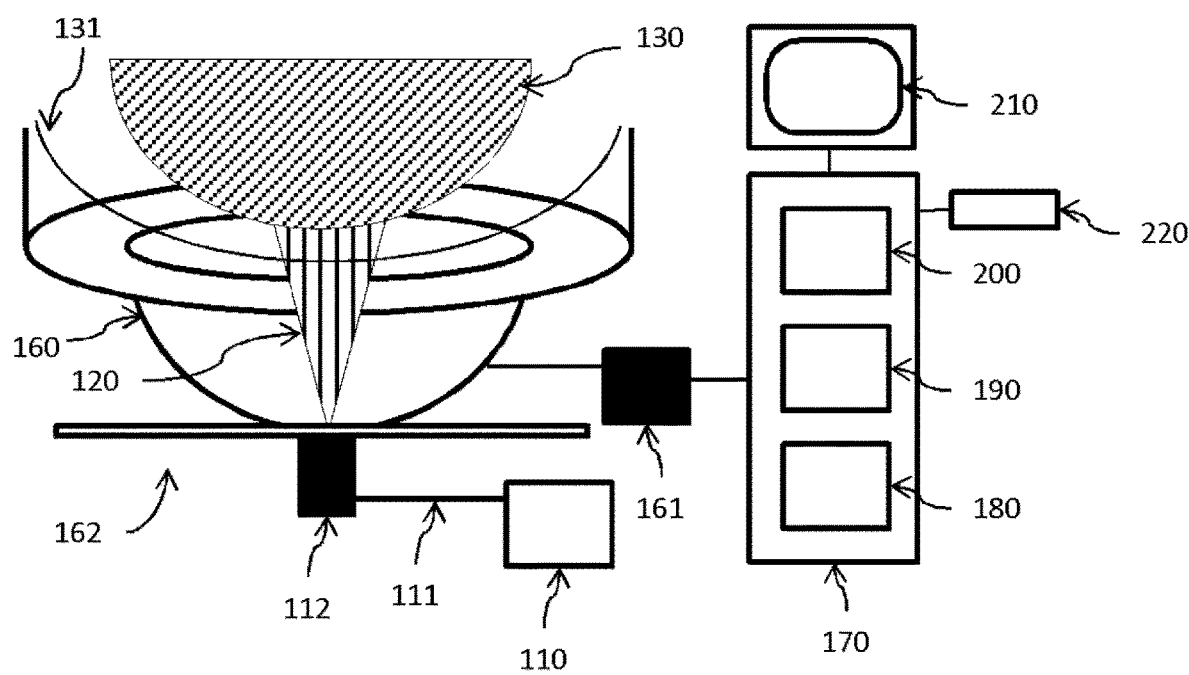
FIG. 3 is an apparatus diagram for explaining Embodiment 1.

The configuration and operation of the apparatus in the present embodiment will be explained next with reference to FIG. 3. Pulsed light 120 emitted by a Ti:sapphire laser 110 passes through an optical bundle fiber 111, strikes an irradiation optical system 112, passes through a mirror, a lens and a diffusion plate, and is projected on the breast 130 of a person, as an object. The pulsed light 120 has a pulse width of 20 nsec, a wavelength of 756 nm and 797 nm, and a frequency of 10 MHz. A bowl-shaped probe 160 is filled with water, and a breast cup 131 made of PET and having a thickness of 300 μm is submerged in the water. Also the inner side of the breast cup 131 is filled with water, so that the breast 130 is submerged in water. Water is used herein for the purpose of acoustic matching, but for instance oil or an ultrasonic gel may be used instead.

Acoustic waves generated in the breast 130 on account of the photoacoustic effect propagate for instance through the water, and thereafter are received by a plurality of piezoelectric elements lined up in the form of a Fibonacci array, in the bowl-shaped probe 160. The piezoelectric elements have a center frequency of 3 MHz and a bandwidth of 80%. The relative position of the bowl-shaped probe 160 and the irradiation optical system 112 with respect to the breast 130 can be modified, in the horizontal direction and the depth direction on the paper, by means of a scanning mechanism 162. Information over a wide area can be acquired thus through measurement of photoacoustic waves while under scanning of pulsed light irradiation positions and acoustic wave reception positions.

An electrical signal (reception signal) derived from the received acoustic waves is amplified, is subjected to digital conversion at a sampling frequency of 20 MHz, and the result is stored in a memory (not shown) in a data acquisition system 161. A workstation 170 being the information processing unit 7 in the present embodiment has a region segmentation unit 200, a sound velocity determining unit 190 and a characteristic information acquisition unit 180.

The region segmentation unit 200 creates a region distribution in which the interior of the breast is segmented into respective segmented regions, namely a mammary gland region, a fat region, and a tumor region. In this case an image may be used which results from deforming an MRI image to the shape of the object at the time of photoacoustic wave measurement. The sound velocity determining unit 190 determines sound velocity at each segmented region in accordance with the method described below. The characteristic information acquisition unit 180 generates a hemoglobin concentration distribution of the interior of the breast by performing reconstruction using a reception signal, on the basis of the arrangement and distribution of the segmented regions and on the basis of sound velocity at each region. The display unit 210 displays an image.

Processing by the workstation 170 will be explained in detail next. Firstly, the region segmentation unit 200 deforms/aligns, with respect to a PAT image, an MRI image being the image resulting from MRI measurement of the object, prior to or subsequently to a PAT measurement. A known method using a singular point such as a nipple on the surface of the object, or a characteristic portion such as a blood vessel branch in the interior of the object, can be resorted to herein for deformation/alignment.

Next, on the basis of the MRI image having undergone deformation/alignment, the sound velocity determining unit 190 creates a region distribution on the basis of input information from the input unit, in accordance with a segmentation method such as threshold value method, a region expansion method, or a SNAKE method. A mammary gland region is extracted using a subtraction image obtained using a contrast agent, in a case where a tumor region is to be extracted using an image resulting from deformation/ alignment of an ordinary MRI image to a PAT image. In the region distribution, a region encompassing the entirety of the breast is subdivided into voxels, and each voxel is labeled so as to distinguish between a mammary gland region, a fat region and a tumor region. In the present embodiment, a fat region is labeled as 1, a mammary gland region is labeled as 2, a tumor region is labeled as 3, and other regions are labeled as 0. A three-dimensional atlas image, an ultrasonic image or a CT image may be used instead of the MRI image having been deformed/aligned to a PAT image.

Image Reconstruction

Figure 5:
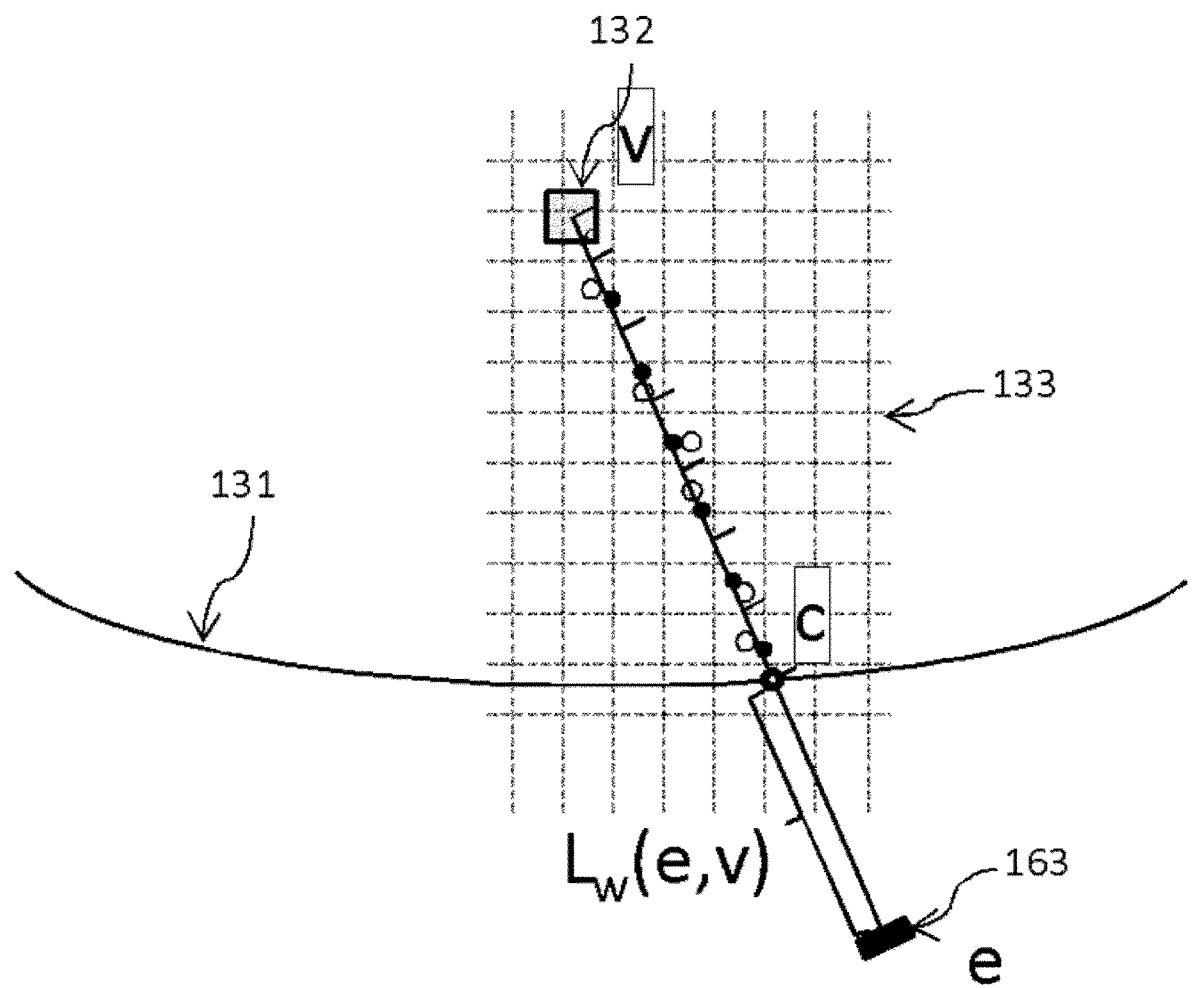
FIG. 5 is an explanatory diagram of reconstruction taking into account a region distribution and sound velocity at each region, in Embodiment 1.

A detailed explanation follows next, with reference to FIG. 5, on reconstruction taking into account a region distribution and sound velocity at each region, in the characteristic information acquisition unit 180. Each object region is divided into a plurality of voxels 133. FIG. 5 illustrates a method for calculating sound velocity that is utilized in order to reconstruct a voxel 132 at coordinates (xv, yv, zv), in a reception signal received at a time where a given element 163 is at coordinates (xe, ye, ze). A voxel group on a two-dimensional plane will be explained herein, for the purpose of simplifying the explanation. Refraction will be disregarded. However, sound rays derived from propagation of acoustic waves undergo refraction according to differences in refractive index between adjacent media, and accordingly it is more preferable that refraction be factored in when determining a propagation path.

The coordinates (xe, ye, ze) of the given element 163 are known beforehand for instance through calibration. The breast cup 131 is shaped as part of a sphere having a radius of 80 mm with respect to a center lying at a certain position. The coordinates of an intersection c of the breast cup 131 and a straight line (over distance L) that joins the coordinates of the element 163 and the coordinates of a reconstruction voxel v can be calculated, since the shape of the breast cup 131 is known. A distance Lw (e, v) between the element 163 and the intersection c can therefore be calculated. The sound velocity over the distance Lw is the sound velocity in an acoustic matching material (water). In the present embodiment the breast is in contact with the breast cup 131.

Next, line segments li over the distance d are sequentially disposed from the intersection c towards the reconstruction voxel v. The sound velocity at the closest voxel to the center coordinates of each line segment li is set as the sound velocity Sli at that line segment. Similarly, for a distance ds resulting from dividing Lw by d, the sound velocity at the voxel closest to the center coordinates is taken as a sound velocity Sls at that line segment. As a result, an average sound velocity S used for reconstructing a signal received by the element 163 can be calculated in accordance with Expression (2) below.

[Math. 2]

$$S = \frac{\left(Sw \cdot Lw + \sum_{i=1}^{N} Sli \cdot d + Sls \cdot ds\right)}{L} \quad (2)$$

In the expression, Sw is sound velocity in water inside the bowl-shaped probe. A sampling position from the reception signal outputted by the element 163 can be determined on the basis of sound velocity Sw and the distance from the element 163 to a voxel of interest. Expression (2) is calculated for all voxels to be reconstructed and for all the elements in the probe, to calculate an average sound velocity in the voxels with respect to the elements. Characteristic information distribution is acquired through image reconstruction using that average sound velocity. Time-domain universal back projection is appropriate herein as the reconstruction method, but other methods may be resorted to. Sampling data from a reception signal may be specified using delay time or a sampling point number, without calculation of average sound velocity, as in Expression (2).

Sound Velocity Determination

A method for determining sound velocity at each segmented region will be explained next with reference to FIG. 6. The breast 130 is divided into a fat region 134, a mammary gland region 135 and a tumor region 136. Firstly, as illustrated in FIG. 6A, a first ROI (region of interest) 137 is designated within the fat region 134, which occupies the region closest to the probe. Sound velocity is estimated using, as an objective function, the sharpness of the image of the interior of a first ROI 137, i.e. the sum total, for all voxels, of the derivative of the image in the x direction and the derivative in the y direction. In this case an identical sound velocity is set for the fat region, the mammary gland region and the tumor region. This sound velocity fits within the numerical value range that fat can take on. Herein the coordinates of the first ROI 137 in the z direction are adjusted in order to prevent offset of image regions in the interior of the first ROI 137 derived from changes in sound velocity. As a result, a blood vessel 140 within the fat region is visualized, as illustrated in FIG. 6B, and the sound velocity Sl in the fat region is determined.

Next, a second ROI 138 is designated in the mammary gland region occupying a region close to the probe, and sound velocity is estimated using an objective function in the form of the sum total, for all voxels, of the sharpness of an image of the interior of the second ROI 138. In this case there is set a same sound velocity, for the mammary gland region and the tumor region, being a sound velocity within a numerical value range of sound velocity that the mammary gland and a tumor can take on. Further Sl is used as the sound velocity in the fat region. As a result, a blood vessel 141 is visualized in the mammary gland region, as illustrated in FIG. 6C and a sound velocity Sg in the mammary gland region is determined.

Lastly a third ROI 139 is designated in the tumor region, and sound velocity is estimated. In this case there is created a plurality of images of the third ROI 139 by modifying the sound velocity of the tumor region 136 in increments of 10 m/sec while using the sound velocity Sl of the fat region and the sound velocity Sg of the mammary gland region. The plurality of images is displayed on the display unit 210, and sound velocity is determined through selection of an optimal image by the user, using the input unit 220. A blood vessel 142 is visualized as illustrated in FIG. 6D. The fat region and the mammary gland region are determined on the basis of image sharpness, and the tumor region is determined through display of a plurality of images with varying sound velocity, and on the basis of an input from an input unit, but sound velocities in the respective regions may be combined once established.

The method for designating the positions of the first through third ROIs 137, 138, 139 may involve designation using the input unit while the user is viewing images displayed on the display unit 210; alternatively, the positions may be determined automatically by the workstation 170.

Processing Procedure

Figure 4:
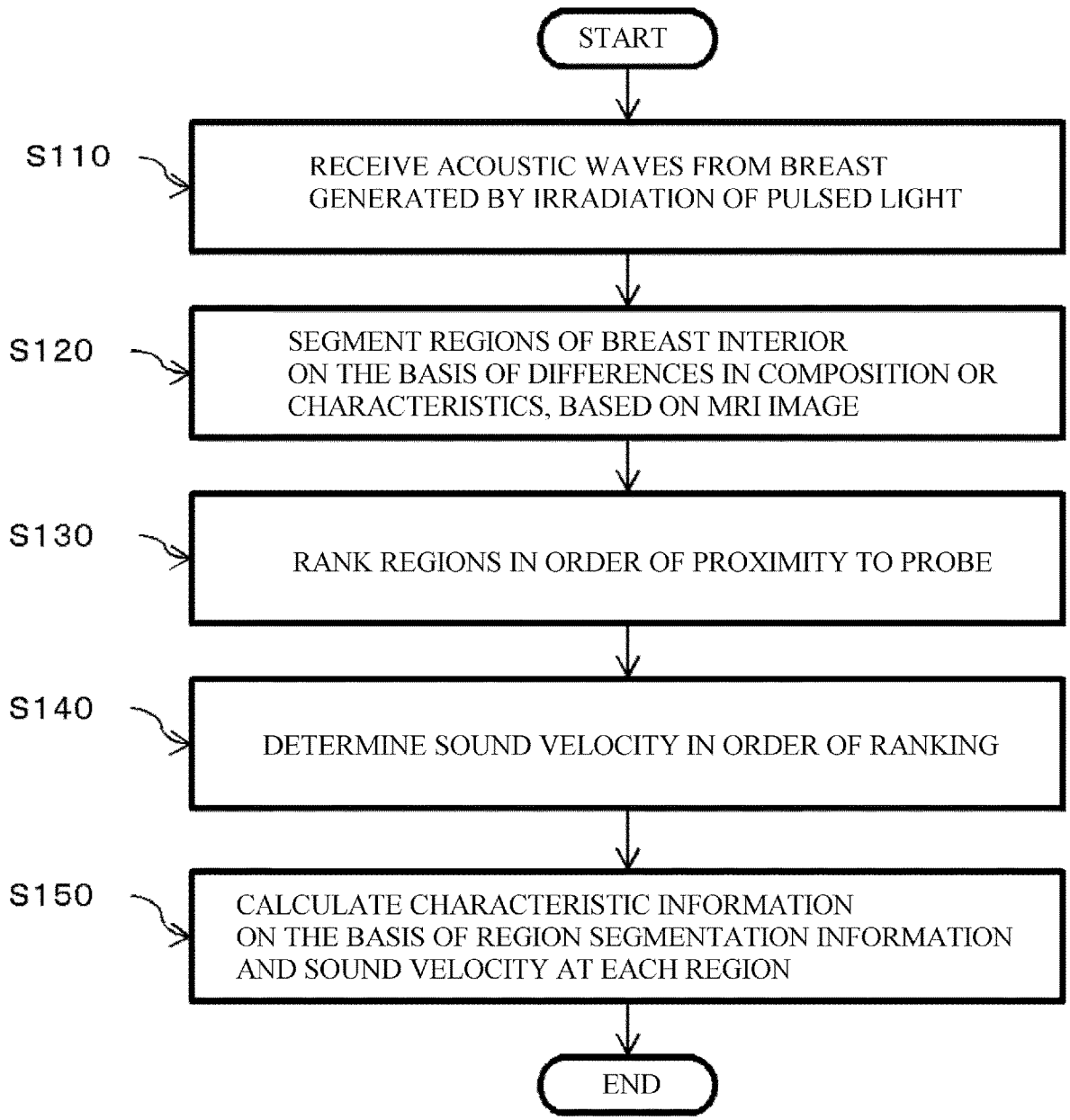
FIG. 4 is a flowchart for explaining Embodiment 1.

An information acquisition method according to the present embodiment will be explained next with reference to the flowchart in FIG. 4.

(Step S110): pulsed light 120 is irradiated to the breast 130, from the irradiation optical system 112. Pulsed light propagating through the interior of the breast is absorbed by hemoglobin in the object, and acoustic waves are generated thereupon on account of the photoacoustic effect. The bowl-shaped probe 160 receives the acoustic waves, and converts the acoustic waves to a reception signal.

(Step S120): to acquire a region distribution, the region segmentation unit 200 segments the interior of the breast into a fat region/mammary gland region/tumor region on the basis of image intensity in an MRI image inputted via the input unit 220.

(Step S130): next, the region segmentation unit 200 establishes from which region a sound velocity is to be determined. Basically, the region segmentation unit 200 determines regions in order of proximity to the bowl-shaped probe 160. Alternatively, the region distribution may be displayed on the display unit 210, and the user may establish a given order through input via the input unit 220.

(Step S140): the sound velocity determining unit 190 determines sound velocity at each segmented region.

(Step S150): the characteristic information acquisition unit 180 performs image reconstruction through adjustment of the delay time of a reception signal from each voxel, received by each element, on the basis of region segmentation information and sound velocity at each segmented region, and calculates characteristic information about the object. As a result, there are calculated an initial sound pressure distribution, an absorption coefficient distribution, and further a hemoglobin concentration distribution and oxygen saturation distribution using spectroscopic information.

Herein sound velocity is determined one segmented region at a time, but the sound velocities of the regions may be estimated all at once, using an objective function that represents a characteristic of an image of all regions, or an image of a deepest region. Other than image sharpness, the plane resemblance, line resemblance or point resemblance of an image can also be used herein as the objective function. A degree of similarity of a corresponding segment in the MRI image may be used as the objective function. Otherwise, any function may be used as the objective function so long as the function allows quantifying visualization of the object to be imaged. For instance, literature values, statistical values, and prior measured values of the subject may be used as the sound velocity in the fat region, the mammary gland region and the tumor region Instead of establishing one sound velocity value for one segmented region, a given segmented region may be further subdivided. Preferably, for instance, a gradient is imparted to sound velocity in the mammary gland region, in accordance with the image intensity of the MRI image.

In the present embodiment the object is segmented into a plurality of regions, and image reconstruction is performed in which there is reflected sound velocity at each segmented region. As a result, it becomes possible to improve the precision of reconstruction using information pertaining to a sound velocity distribution, in photoacoustic tomography.

Embodiment 2

In the present embodiment there is used a 1D array probe of handheld type for both reception of ultrasonic waves and reception of photoacoustic waves. The boundaries between segmented regions are approximated with convex geometric shapes. To generate and display an image, image reconstruction is performed in real time in accordance with an input by the user, for the sound velocity value of each segmented region.

Configuration and Operation

Figure 7:
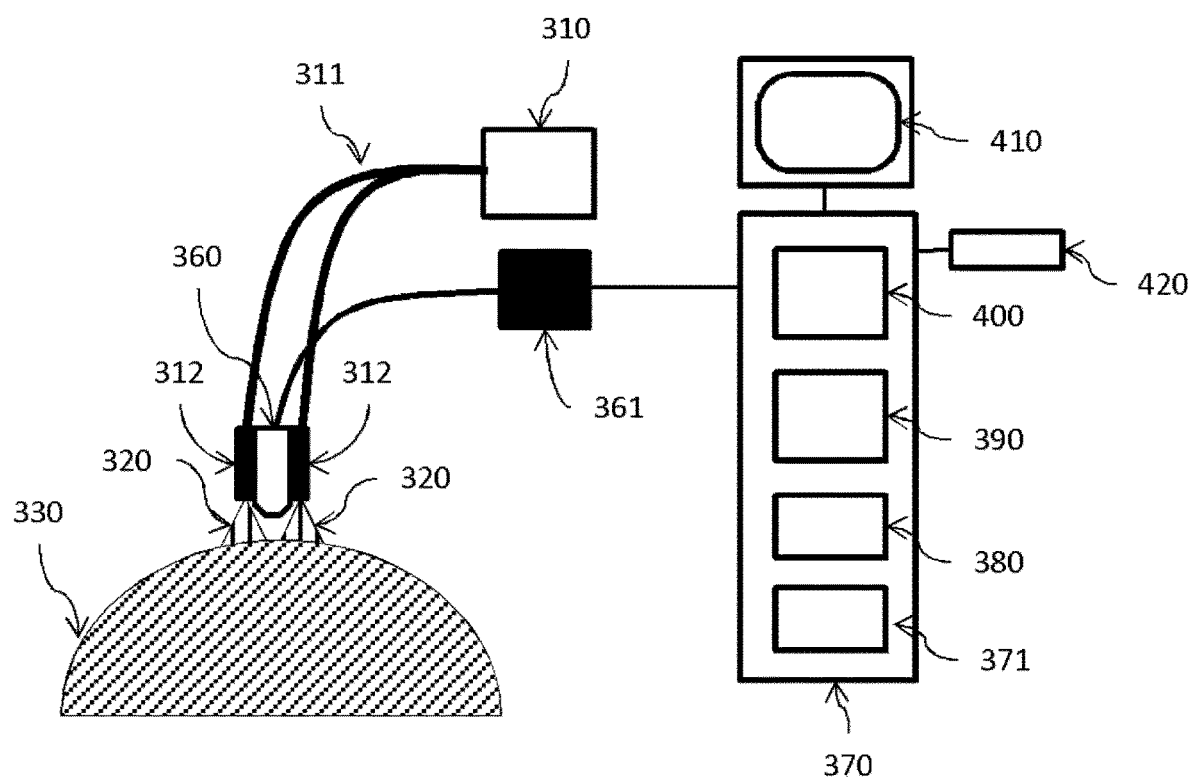
FIG. 7 is an apparatus diagram for explaining Embodiment 2.

The configuration and operation of the apparatus in the present embodiment will be explained next with reference to FIG. 7. Pulsed light 320 of 797 nm emitted by an OPO laser 310 passes through an optical bundle fiber 310, is expanded by a lens and scattered by a diffusion plate in an irradiation optical system 312, and is then irradiated onto a breast 330 being the object. The irradiated pulsed light is scattered in and propagates through the interior of the breast 330, and is converted to acoustic waves by an absorbing body on account of the photoacoustic effect.

Herein a 1D array probe 360 has a plurality of elements arrayed linearly, and light output ends arrayed on both sides. Photoacoustic waves generated by the absorbing body are converted to an electrical signal by the 1D array probe 360, are thereafter amplified and subjected to digital conversion in a signal converter 361, and the result is stored in a memory (not shown) in the form of a photoacoustic reception signal. In the present embodiment a handheld probe is used, and accordingly measurements are performed not using a cup for breast holding, but by coating the object with a gel for ultrasonic wave transmission.

Further, the 1D array probe 360 has the function of focusing and transmitting ultrasonic waves onto the breast 330, and receiving the reflected ultrasonic waves (echo waves). The received echo waves are converted to an electrical signal, are amplified and subjected to digital conversion by the signal converter 361, and the result is stored as a reflected ultrasonic wave reception signal in a memory (not shown). The denominations "ultrasonic waves" and "echo waves" will be used, as needed, to clearly distinguishing the foregoing from photoacoustic waves, but these terms are not meant to limit the wavelength of the waves. An element for photoacoustic reception and an element for ultrasonic wave transmission/reception may be identical, as in the present embodiment, or may be different.

A workstation 370 being the information processing unit 7 in the present embodiment has a region segmentation unit 400, a sound velocity determining unit 390, a characteristic information acquisition unit 380 and an ultrasonic image creation unit 371.

The workstation 370 acquires the photoacoustic reception signal and the reflected ultrasonic wave reception signal stored in a memory in the signal converter 361. The ultrasonic image creation unit 371 generates an ultrasonic image using the reflected ultrasonic wave reception signal. The region segmentation unit 400 acquires a region distribution through segmentation of the object into a mammary gland/ fat region and into a tumor region, using the image intensity of the ultrasonic image.

The sound velocity determining unit 390 determines sound velocity at each segmented region. Herein the user may utilize a value inputted from an input unit 420. The characteristic information acquisition unit 380 performs image reconstruction on the basis of the photoacoustic reception signal, using the region segmentation information and sound velocity information, and calculates a hemoglobin concentration distribution. The calculated hemoglobin concentration distribution is displayed on the display unit 410.

Upon input of sound velocity at each segmented region by the user, via the input unit 420, image reconstruction reflecting the inputted values is carried out in real time, and a resulting image is displayed on the display unit 410. Sound velocity values can be set as a result with good precision. Respective constraints may be placed on the values that can be inputted through the input unit 420, on the basis of a numerical value range expected for each segmented region. Alternatively, a warning may be displayed in case that there is inputted an impossible numerical value for a given segmented region. Further, there may be provided a function for enabling saving of a snapshot of the image displayed in real time, together with region segmentation information, sound velocity information at each region, and the ultrasonic image reconstructed using the foregoing information items.

The ultrasonic image creation unit 371 has an image creation function of ordinary ultrasonic waves apparatus, and can create at least one kind of image among ultrasonic wave reflection images, elastographic images, and Doppler images. The region segmentation unit 400 extracts a portion the contrast of which with respect to the surroundings is significant at the time of segmentation of an ultrasonic reflection image. Herein region boundaries are approximated with convex geometric shapes. In the present embodiment regions are segmented as lying outward or inward of a given convex geometric shape. To this end, a numerical expression denoting the geometric shape and an associated with region name are saved as the region segmentation information. The calculation time of the average sound velocity between voxels and elements can be shortened as a result.

The input unit that feeds sound velocity values to the sound velocity determining unit 390 is provided with knobs corresponding to the segmented regions. A label is attached to each segmented region displayed on the display unit 410. The user inputs the sound velocity value through turning of a respective knob corresponding to the label. One knob may be used while being switched by a switch.

The characteristic information acquisition unit 380 will be explained in detail next. An explanation follows next, with reference to FIG. 9, on a sound velocity calculation method used for reconstruction of a voxel 333 having coordinates (xv, yv, zv), at a time where an element 363 included in a linear array is positioned at coordinates (xe, ye, ze). A voxel group on a given two-dimensional plane will be explained herein, for the purpose of simplifying the explanation. Refraction will be disregarded.

Figure 9:
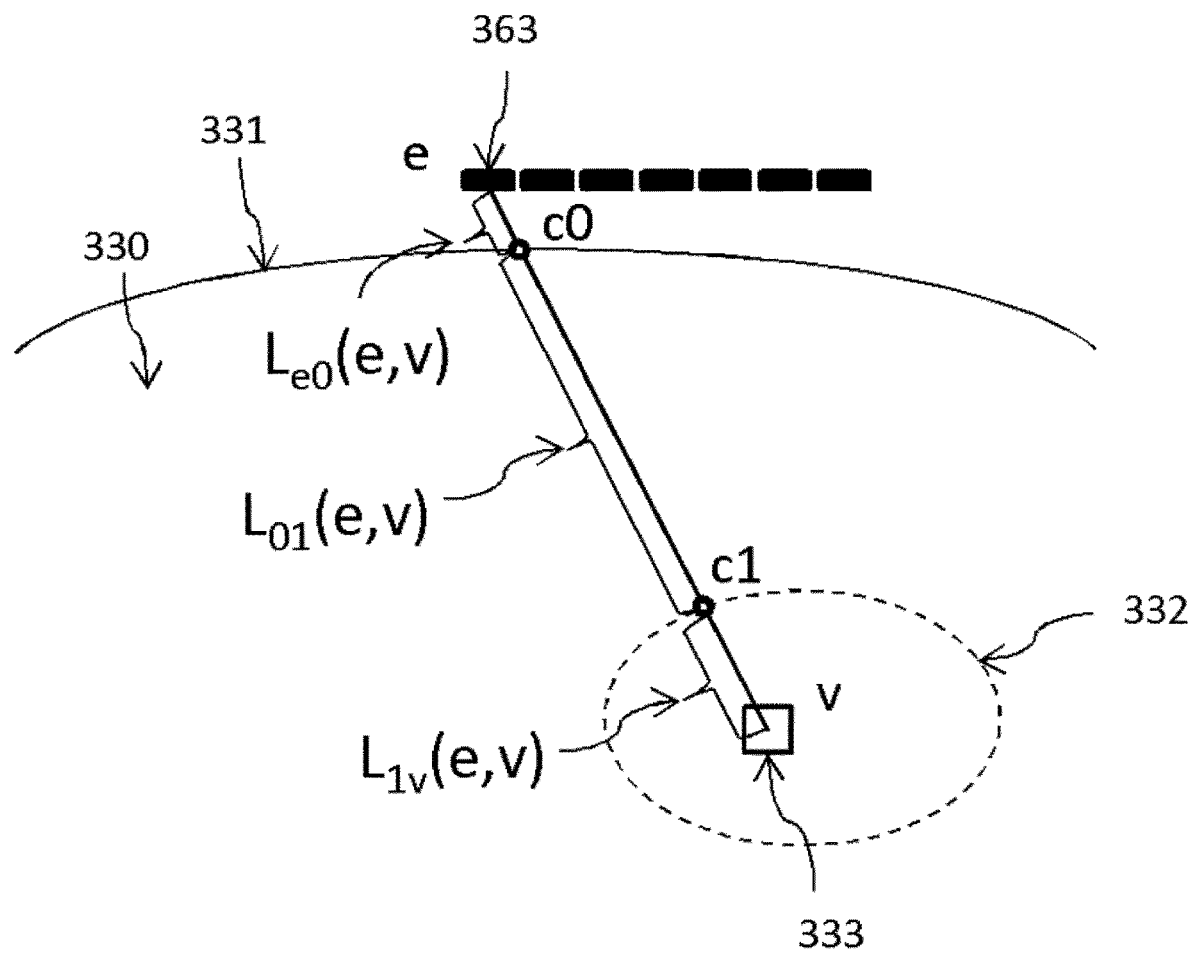
FIG. 9 is an explanatory diagram of reconstruction taking into account a region distribution and sound velocity at each region, in Embodiment 2.

The geometric shape representing the boundary of the surface 331 of the object and the tumor region 332 is mathematized beforehand in the region segmentation unit 400. The characteristic information acquisition unit 380 calculates an intersection between the geometric shape and a line segment joining the element 363 and the voxel 333, and determines which segmented region each voxel is included in, on the basis of the positional relationship between each voxel and the intersection. In FIG. 9, the intersection between an elliptical tumor region 332 and a line segment is c1. The intersection between the parabolic surface 331 of the object and the line segment is c0. A line segment distance Le0 in a gel region, a line segment distance L01 in the fat and mammary gland region, and a line segment distance L1v in the tumor region are determined by intersection coordinates, voxel coordinates and element coordinates. Sound velocity used in a reception signal by the element 363 during reconstruction of the voxel 333 is calculated on the basis of Expression (3) below, where Sg, Sl and Sc denote respectively set sound velocities of gel, fat and mammary gland, and tumor.

[Math. 3]

$$S = \frac{(Sg \cdot Le0 + Sl \cdot L01 + Sc \cdot L1v)}{L} \quad (3)$$

In the expression, L is the length of a line segment between the voxel 333 and the element 363. An average sound velocity is calculated herein, but there may be calculated a sampling position based on the reception signal of the element 363. Otherwise, any method may be resorted to so long as the method allows for reconstruction in which sound velocity at each segmented region is reflected. A more accurate reflection ultrasonic image can be acquired using sound velocity at each segmented region. The segmented region may be deformed temporarily to an easily calculable shape in a case where the segmented regions are hard to approximate to a geometric shape that is easy to calculate. In this case, a respective segment distance is calculated for the deformed shape, followed by correction of the distance on the basis of a deformation rate of each line segment. Segmented regions can be calculated easily by using the line segment distance in Expression (3).

Processing Procedure

Figure 8:
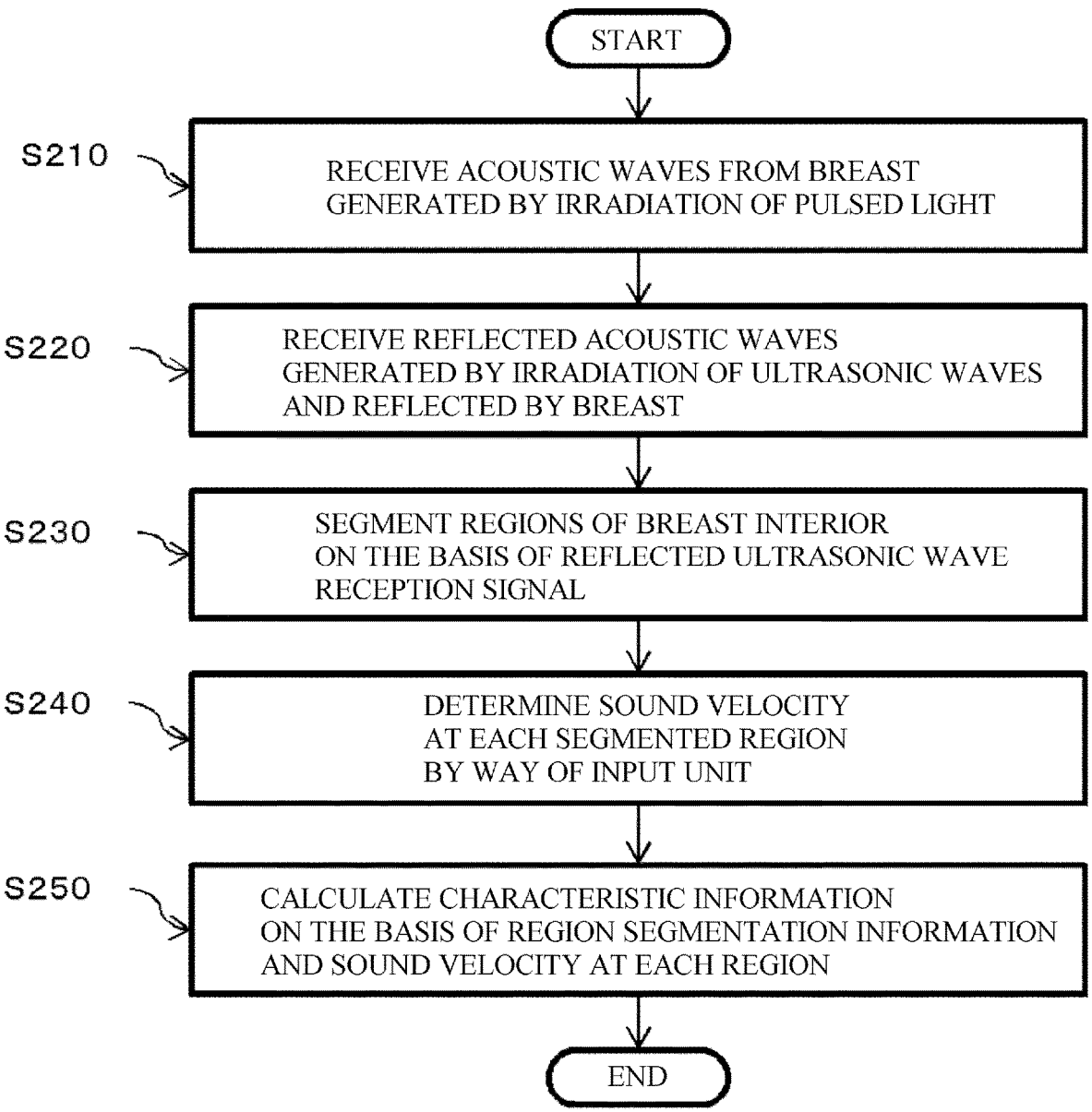
FIG. 8 is a flowchart for explaining Embodiment 2.

An information acquisition method according to the present embodiment will be explained next with reference to the flowchart in FIG. 8.

(Step S210): pulsed light 320 is irradiated to the breast 330, from the irradiation optical system 312. Pulsed light propagating through the interior of the breast is absorbed by hemoglobin in the object, and photoacoustic waves are generated thereupon on account of the photoacoustic effect. The 1D array probe 360 receives the photoacoustic waves and converts the waves to a photoacoustic reception signal.

(Step S220): the 1D array probe 360 transmits ultrasonic waves focused at respective positions inside the breast 330, and receives echo waves being reflected and returning ultrasonic waves. A reflected ultrasonic wave signal is acquired as a result.

(Step S230): the ultrasonic image creation unit 371 creates a reflection ultrasonic image of the interior of the breast on the basis of the reflected ultrasonic wave reception signal. Next, the region segmentation unit 400 segments the interior of the breast into a plurality of regions, on the basis of contrast in the ultrasonic image.

(Step S240): the sound velocity determining unit 390 determines sound velocity at each segmented region using the input unit information.

(Step S250): The characteristic information acquisition unit 380 reconstructs the photoacoustic reception signal on the basis of region segmentation information and sound velocity at each region, and calculates a characteristic information distribution such as a hemoglobin concentration distribution. In this case sound velocity that reflects tissue features is used for delay time calculation, and therefore measurement precision is improved also in handheld-type apparatus. The shape of each segmented region can be calculated easily through approximation to a geometric shape.

Embodiment 3

An apparatus of the present embodiment is substantially similar to that of Embodiment 1, but herein a planar semi-absorber film can be disposed at a position onto which pulsed light is irradiated. It becomes possible thereby to irradiate both the object and the semi-absorber film with pulsed light. As a result, plane waves are generated from the semi-absorber film. Some of the plane waves strike the breast, and are reflected in the interior of the breast, becoming echo waves. The apparatus in the present embodiment receives the echo waves by way of a bowl-shaped probe, to thereby create an ultrasonic image and to segment regions of the interior of the breast. The apparatus in the present embodiment, moreover, segments a vasculature region on the basis of a hemoglobin distribution obtained from the photoacoustic reception signal, and assigns a sound velocity of blood.

Configuration and Operation

Figure 10:
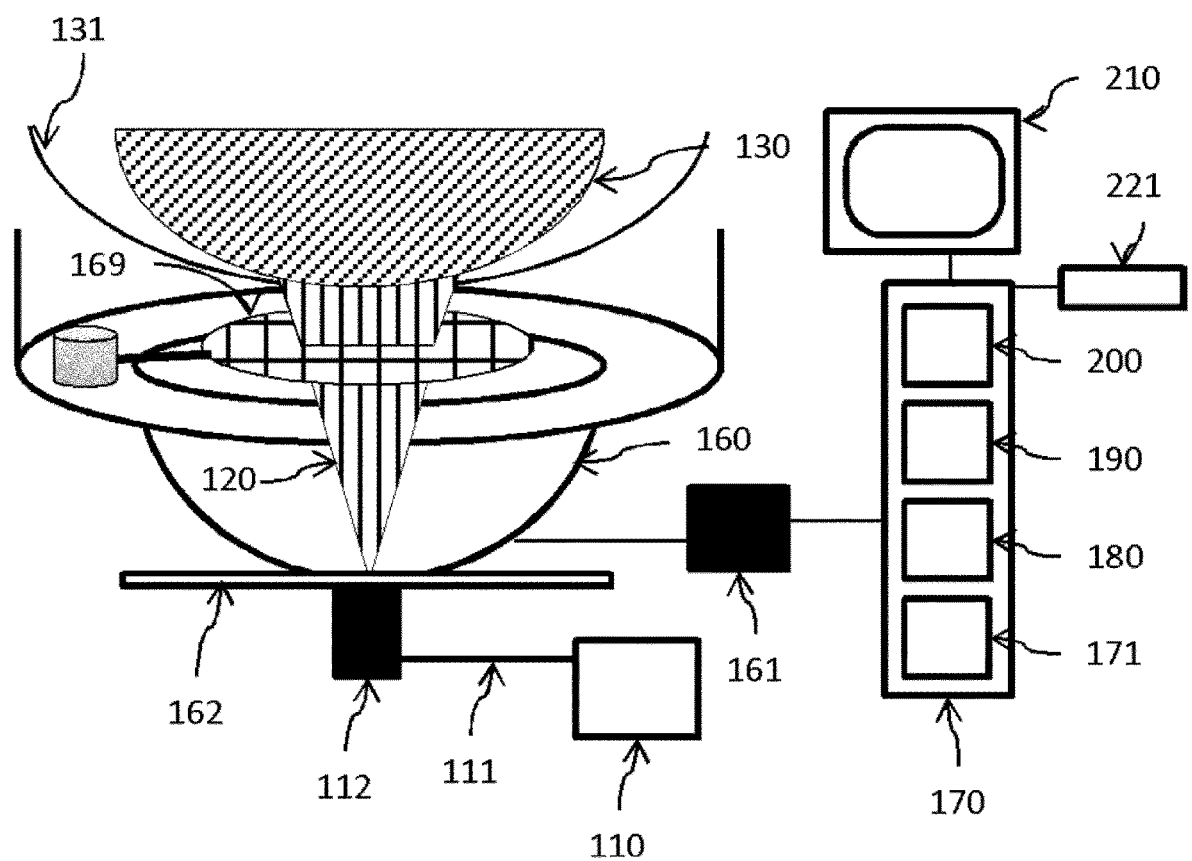
FIG. 10 is an apparatus diagram for explaining Embodiment 3.

The configuration and operation of the apparatus of the present embodiment will be explained, with reference to FIG. 10, focusing on the portion specific to the present embodiment. A semi-absorber film 169 is disposed at a position traversed by pulsed light 120, between the irradiation optical system 112 and the object 130. The semi-absorber film absorbs part of the pulsed light 120 irradiated from the irradiation optical system 112, and generates acoustic waves on account of the photoacoustic effect, while allowing part of the pulsed light 120 to reach the breast 130. A material having acoustic impedance close to that of water and having a Grüneisen parameter as large as possible is preferably used herein as the material of the semi-absorber film 169. For instance, a gelatin sheet or TPX sheet is appropriate herein. The semi-absorber film 169 preferably has a thickness such that there are generated photoacoustic waves in a band close to the center frequency of the elements that are disposed in the bowl-shaped probe 160. The thickness of the semi-absorber film 169 is set to about 0.5 mm in a case where the center frequency of the elements in the bowl-shaped probe 160 is 3 MHz.

The bowl-shaped probe 160 receives the photoacoustic waves, and converts the photoacoustic waves to a photoacoustic reception signal. A workstation 170 being the information processing unit 7 in the present embodiment has a region segmentation unit 200, a sound velocity determining unit 190, a characteristic information acquisition unit 180 and a reflection signal imaging unit 171.

Figure 12:
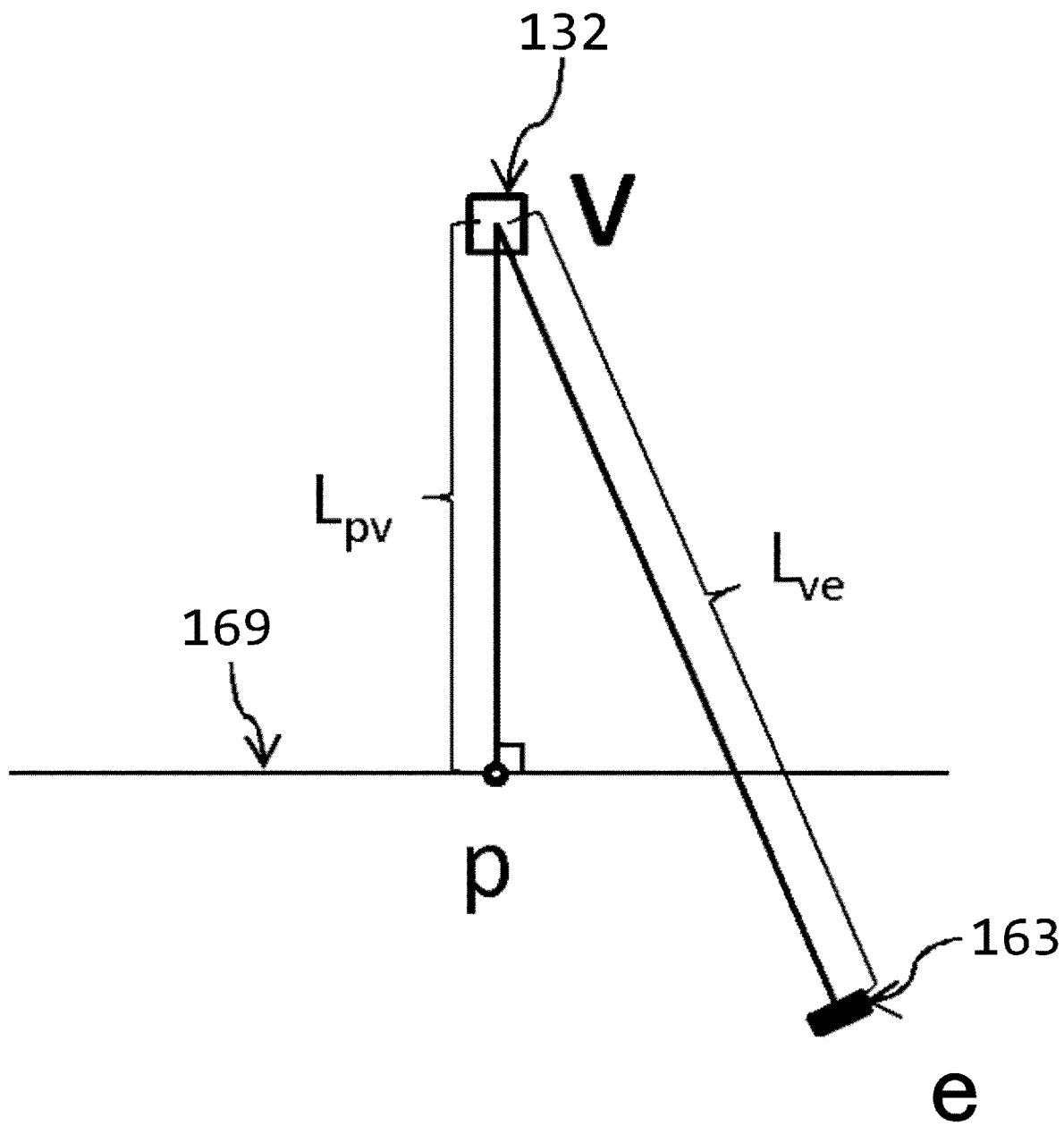
FIG. 12 is a calculation method in a reflection signal imaging unit of Embodiment 3.

The reflection signal imaging unit 171 converts the photoacoustic reception signal to distribution data. The method involved will be explained with reference to FIG. 12. The plane waves generated by the semi-absorber film 169 are scattered in a voxel 132, and are received as reflected ultrasonic waves by the element 163. Herein p denotes the base of a perpendicular line from the voxel 132 to the semi-absorber film. Thus photoacoustic waves propagate over a distance Lpv+Lve, along the path point p→point v→point e. In reconstructing the voxel 132, a sampling number for the reception signal by the element 163 can be determined on the basis of the propagation time of the photoacoustic waves. A reflection signal image can be created by performing similar processing on combinations of respective voxels and elements.

The region segmentation unit 200 segments the reflection signal image into a fat and mammary gland region, and a tumor region, on the basis of image contrast. The sound velocity determining unit 190 works out sound velocity from segmented regions in order of proximity to the bowl-shaped probe 160. The characteristic information acquisition unit 180 calculates a hemoglobin distribution through image reconstruction using the region segmentation information and sound velocity at each segmented region, and displays the hemoglobin distribution on the display unit 210.

Preferably, the reflection signal image is re-created using the region segmentation information and sound velocity at each segmented region. The precision of the reflection signal image is improved as a result. Region segmentation and sound velocity determination are preferably carried out once more using the reflection signal image of improved precision. The image quality of the reconstruction image improves as this process is repeated.

Further, a vasculature region may be extracted from the object, on the basis of the hemoglobin distribution, and reconstruction may be performed using a sound velocity value of blood for that vasculature region.

Processing Procedure

Figure 11:
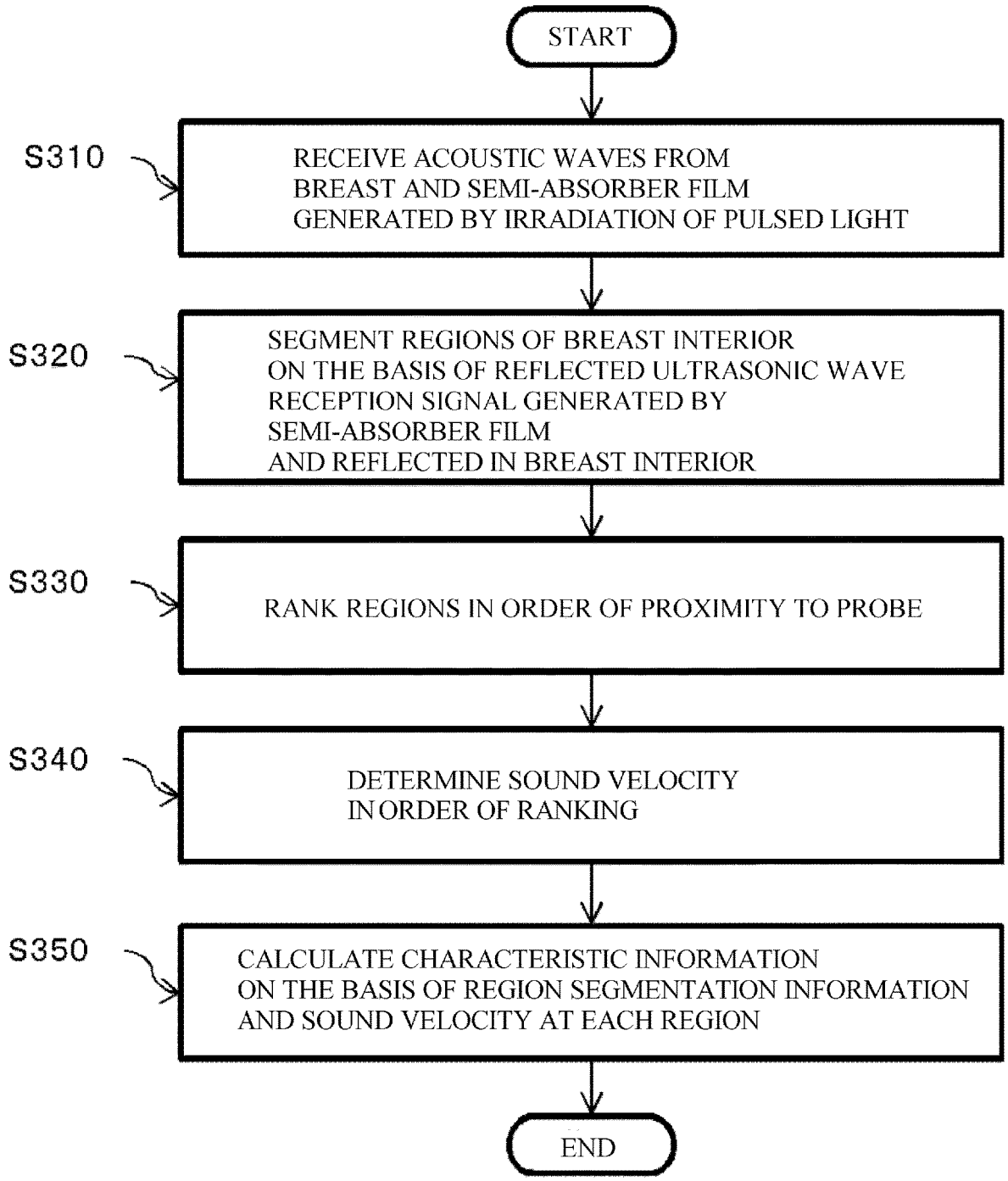
FIG. 11 is a flowchart for explaining Embodiment 3.

An information acquisition method according to the present embodiment will be explained next with reference to the flowchart in FIG. 11.

(Step S310): pulsed light 120 is irradiated from the irradiation optical system 112. Part of the pulsed light 120 is absorbed by the semi-absorber film 169, which results in generation of photoacoustic waves (transmission ultrasonic waves). The transmission ultrasonic waves are reflected on account of the acoustic impedance of the interior of the breast, and become reflected ultrasonic waves. The rest of the pulsed light 120 passes through the semi-absorber film 169, and is absorbed by hemoglobin in the interior of the object, whereupon photoacoustic waves are generated. The bowl-shaped probe 160 receives the photoacoustic waves and reflected ultrasonic waves, converts the foregoing to a photoacoustic reception signal and a reflected ultrasonic wave reception signal, respectively, and outputs the resulting signals.

(Step S320): the reflection signal imaging unit 171 creates a reflection signal image from the reflected ultrasonic wave reception signal, and sets a plurality of segmented regions in the interior of the breast on the basis of image contrast.

(Steps S330 to 340): the sound velocity determining unit 190 prescribes an order, in sequential proximity to the probe, for the plurality of segmented regions. Next, sound velocity at each segmented region is determined according to the prescribed order.

(Step S350): the characteristic information acquisition unit 180 performs reconstruction in which a sound velocity distribution is taken into account, in accordance with the region segmentation information and sound velocity at each segmented region. The above flow enables region segmentation using an ultrasonic image derived from ultrasonic waves, generated by the semi-absorber film, also in a case where the probe does not have an ultrasonic wave transmission/reception function. Precision in image reconstruction using sound velocity is improved as a result.

Embodiment 4

The apparatus in the present embodiment performs a measurement while under automatic mechanical scanning of a handheld probe. The measurement target is herein the hand of a subject. A high-bandwidth element and a low-bandwidth element are linearly juxtaposed alternately in the 1D array probe 560 of the present embodiment. The workstation 570 acquires a large structure inside the hand, using a signal acquired using the low-bandwidth elements, and segments regions of the interior of the hand.

Configuration and Operation

Figure 13:
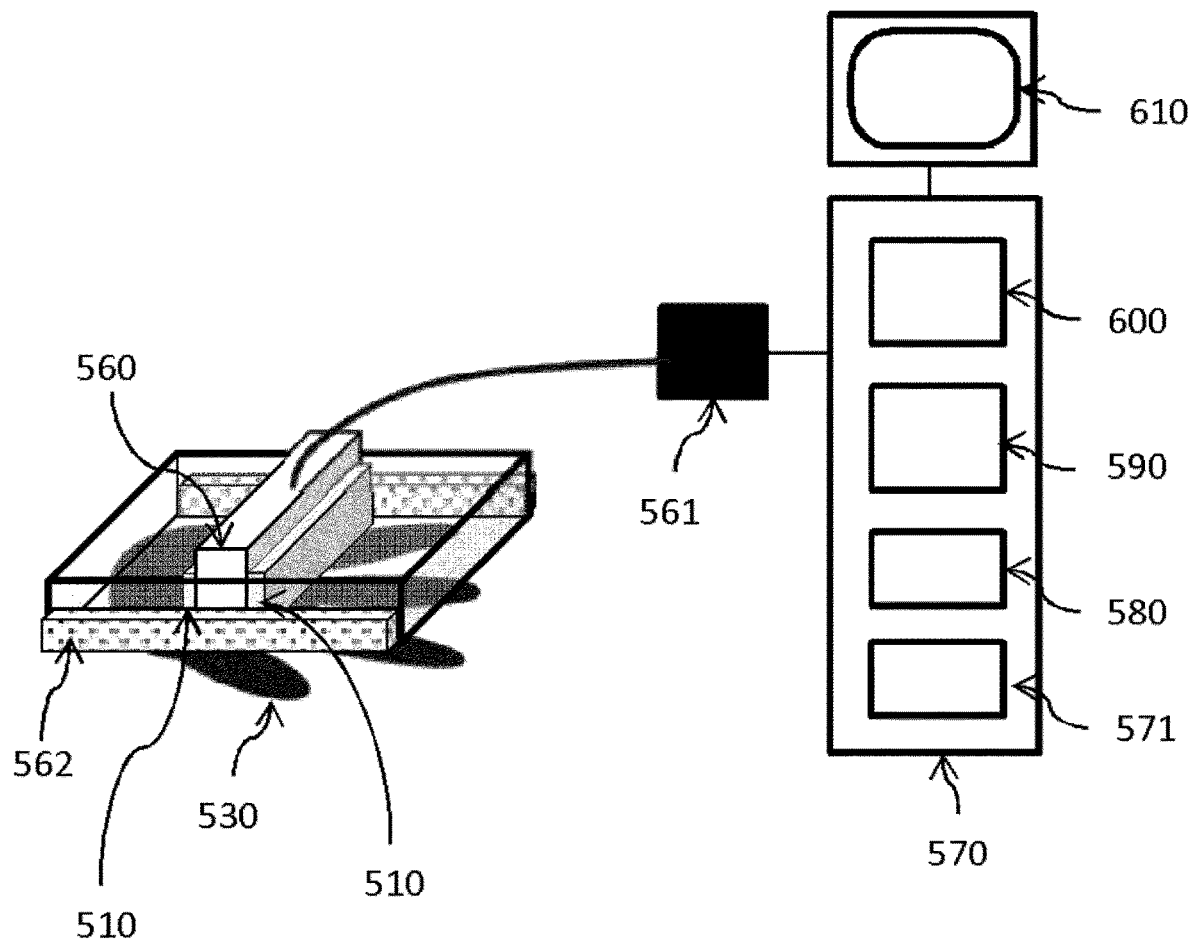
FIG. 13 is an apparatus diagram for explaining Embodiment 4.

The configuration and operation of the apparatus in the present embodiment will be explained next with reference to FIG. 13. The irradiation optical system 510 irradiates a hand 530, being the object, with pulsed light 120 of 797 nm wavelength, outputted from an LED (not shown). The pulsed light 120 is absorbed by an absorbing body in the interior of the hand 530, and photoacoustic waves are generated thereupon. The 1D probe 560 receives photoacoustic waves while being moved by the scanning mechanism 562, and converts the photoacoustic waves to an electrical signal. The 1D probe 560 is a linear array probe in which piezoelectric elements (low-frequency elements) having a center frequency band of 2 MHz and piezoelectric elements (high-frequency elements) having a center frequency band of 9 MHz are arrayed alternately. The signals received by the 1D probe 560 are amplified and digitized, and are stored as a low-frequency element reception signal and a high-frequency element reception signal, in a memory (not shown) of a signal converter 561.

The workstation 570 is provided with a region segmentation unit 600, a sound velocity determining unit 590, a characteristic information acquisition unit 580 and a low-frequency image creation unit 571. The low-frequency image creation unit 571 converts the low-frequency element reception signal to a low-bandwidth image by time-domain universal back projection. The region segmentation unit 600 segments regions using the low-bandwidth image. The sound velocity determining unit 590 determines the sound velocity in order of proximity to the 1D probe 560. The characteristic information acquisition unit 580 calculates hemoglobin concentration in the interior of the hand on the basis of the region segmentation information and sound velocity at each segmented region.

Processing Procedure

Figure 14:
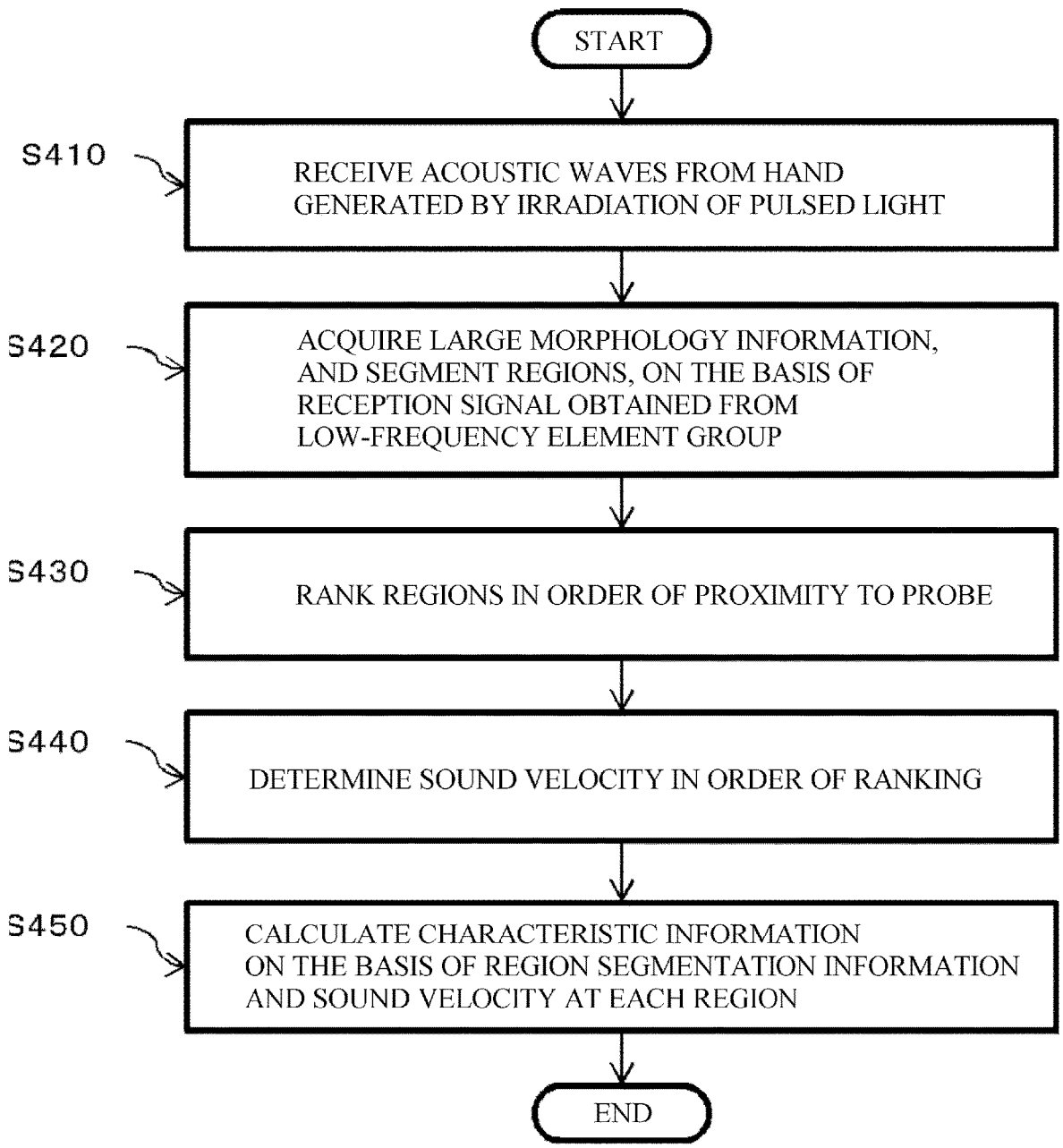
FIG. 14 is a flowchart for explaining Embodiment 4.

An information acquisition method according to the present embodiment will be explained next with reference to the flowchart in FIG. 14.

(Step S410): pulsed light is irradiated from the irradiation optical system 510 to the hand 530, and photoacoustic waves propagate thereupon from the interior of the hand. The low-frequency elements and the high-frequency elements of the 1D probe 560 receive a low-frequency component and a high-frequency component of the photoacoustic waves, and output a low-frequency element reception signal and a high-frequency element reception signal, respectively.

(Step S420): the low-frequency image creation unit 571 creates a low-frequency image through image reconstruction using the low-frequency element reception signal. Low-frequency acoustic waves are less likely to undergo refraction or scattering while propagating than high-frequency acoustic waves, and accordingly are suitable for imaging of comparatively large morphologies in the interior of the object. Therefore, the region segmentation unit 600 acquires large morphology information about the interior of the hand, on the basis of contrast in the low-frequency image, and performs region segmentation.

(Step S430): next, the region segmentation unit 600 ranks the segmented regions according to the distance from the surface scanned by the 1D probe 560.

(Steps S440 to S450): The sound velocity determining unit 590 determines sound velocity at each region, according to a given order. Next, the characteristic information acquisition unit 580 performs image reconstruction taking into account a sound velocity distribution, on the basis of the region segmentation information and sound velocity at each segmented region, and calculates characteristic information. Herein there may be used the high-frequency element signal alone, or both the high-frequency element signal and the low-frequency element signal.

In the above method a reception signal for region segmentation of the interior of the object and a reception signal for imaging of the interior of the object can be acquired in one measurement, and hence the time required for processing can be shortened.

Embodiment 5

In the present embodiment the apparatus configuration is substantially identical to that of Embodiment 1, but the method for segmenting regions in the interior of the object and the sound velocity calculation procedure are different from those of Embodiment 1.

Configuration and Operation

Figure 15:
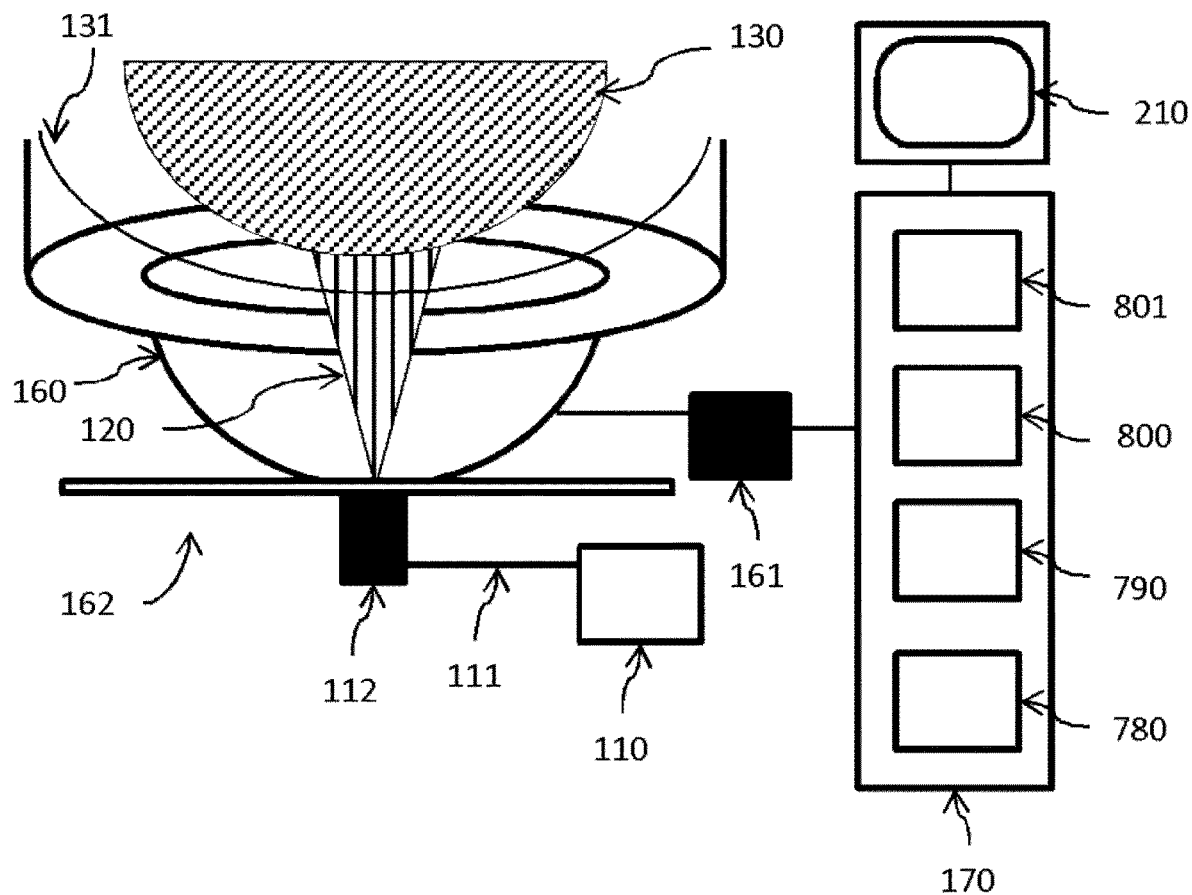
FIG. 15 is an apparatus diagram for explaining Embodiment 5.

The configuration and operation of the apparatus in the present embodiment will be explained next with reference to FIG. 15, focusing on differences with respect to Embodiment 1. The workstation 170 in the present embodiment is provided with a ROI determining unit 801, a region segmentation unit 800, a sound velocity determining unit 790 and a characteristic information acquisition unit 780. The ROI determining unit 801 sets a ROI in the interior of the object, on the basis of an image resulting from reconstruction of a reception signal according to a certain sound velocity.

The sound velocity determining unit 790 in the present embodiment determines sound velocity in that ROI. Specifically, a given sound velocity is set and upon image reconstruct of a ROI, the set value is deemed to be the sound velocity in a case where a blood vessel in the ROI can be imaged at a density equal to or higher than a predetermined threshold value. On the other hand, the set value of sound velocity is modified in a case where the blood vessel is imaged at a lower density than a predetermined threshold value, at the set sound velocity. This processing is repeated to thereby set a sound velocity for the entire region that is to be imaged.

Processing Procedure

Figure 16:
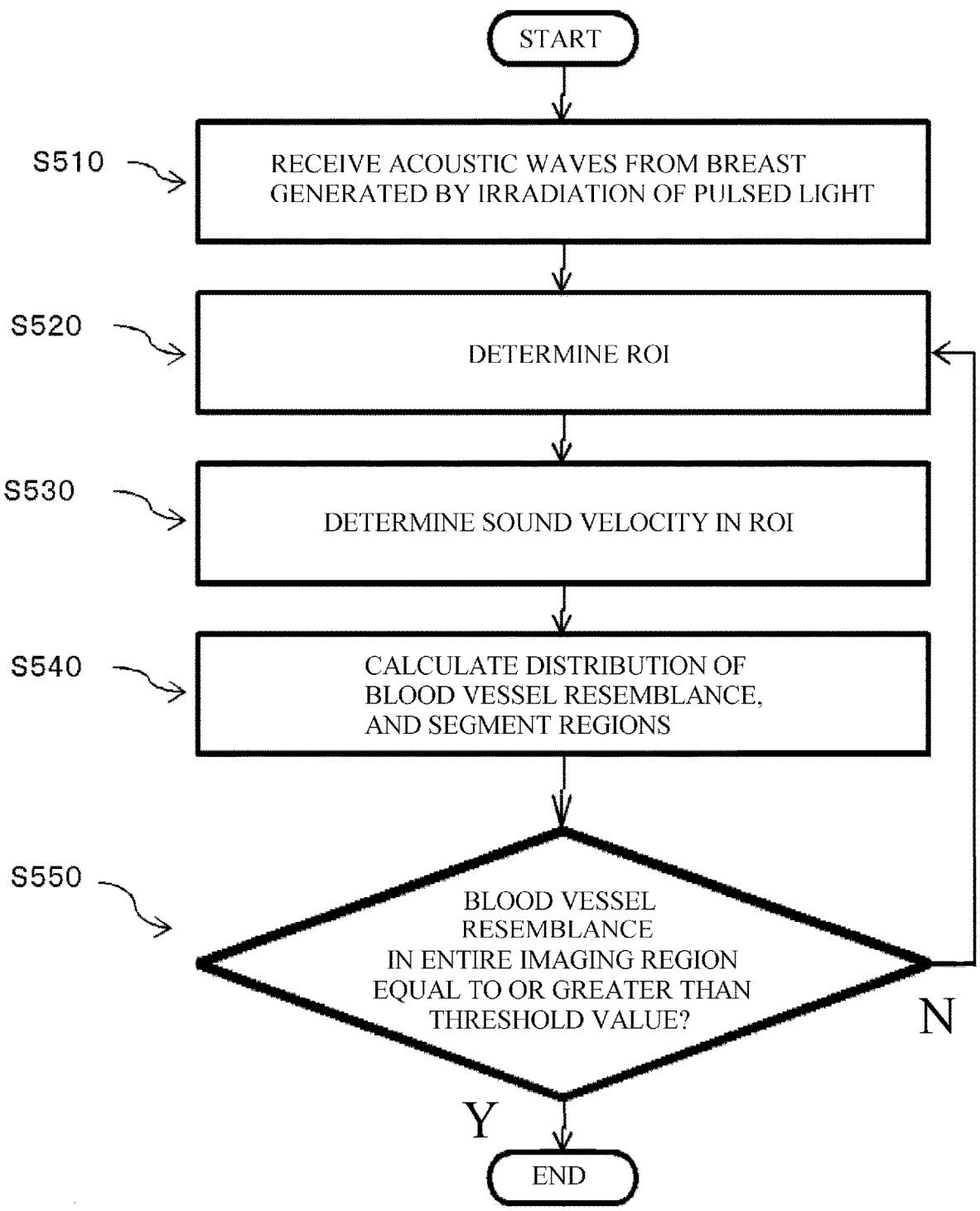
FIG. 16 is a flowchart for explaining Embodiment 5.

The flow in the present embodiment will be explained next with reference to FIG. 16 and FIG. 17.

(Step S510): pulsed light is irradiated onto a breast, and photoacoustic waves are received. The details of this process are identical to those in Embodiment 1.

(Step S520): the ROI determining unit 801 determines a ROI in the interior of the breast. The ROI determining unit 801 firstly sets a ROI 737 at a position comparatively close to the probe in the interior of the breast 130, as illustrated in FIG. 17A.

(Step S530): the sound velocity determining unit 590 determines the sound velocity in the set ROI 737. The line resemblance of the ROI 737 is calculated while the sound velocity in the breast as a whole is modified uniformly, and the sound velocity for which line resemblance is maximal is determined as the sound velocity. Herein line resemblance is evaluated in accordance with the method described in NPL 1.

(Step S540): the region segmentation unit 800 calculates a vascular density distribution of blurred line resemblance, of the interior of the breast, as illustrated in FIG. 17E, on the basis of an image for which line resemblance has been calculated, as in FIG. 17B, and performs segmentation into a region in which vascular density exceeds a given threshold value and a region in which that is not the case. Specifically, the region segmentation unit 800 determines a boundary between regions, on the basis of information indicating blood vessel density.

(Step S550): it is deemed whether line resemblance in the entire imaging region is equal to or higher than a threshold value.

Processing is terminated if the vascular density in the entire region to be imaged is equal to or higher than a given threshold value. If the region to be imaged has therein a portion of lower vascular density than the threshold value, processing in S520 to S550 is repeated.

An explanation follows next on an instance where the processing from S520 to S550 is repeated. The ROI determining unit 801 sets a ROI 738 at a position comparatively close to the probe, in a region have an undetermined sound velocity (region of vascular density lower than a threshold value), as illustrated in FIG. 17B. The sound velocity determining unit 790 determines sound velocity such that the line resemblance of the ROI 738 is maximal.

The region segmentation unit 800 calculates a vascular density distribution of blurred line resemblance, such as the one illustrated in FIG. 17F, on the basis of an image for which there has been calculated a line resemblance in a sound velocity undetermined region, as illustrated in FIG. 17C, and segments regions having vascular density equal to or higher than a given threshold value, and regions having vascular density lower than the threshold value. The threshold value may be different from the above-described threshold value. For instance, the threshold value may be modified depending on the type of tissue (mammary gland, fat or tumor).

The determination in S550 is performed again next. If the entirety of the imaging region is not equal to or higher than the threshold value, the process returns to S520. The region segmentation unit 800 sets, as a ROI, a region 739 in which vascular density is equal to or lower than a given threshold value, as illustrated in FIG. 17C, and determines sound velocity such that the line resemblance within the ROI is maximal.

The region segmentation unit 800 calculates a vascular density distribution of blurred line resemblance, as in FIG. 17G, and segments a region in which vascular density is equal to or higher than a given threshold value, and a region where the vascular density is lower than a threshold value. In the present embodiment, the vascular density in the entire imaging region becomes equal to or higher than the threshold value as a result of the above processing, whereupon the process is accordingly terminated.

Sound velocity is determined herein on the basis of whether or not an objective function takes on a value equal to or higher than a predetermined threshold value. However, segmented regions may be displayed on the display unit 210, in each step, and the user may designate sound velocity at each segmented region using the input unit.

Embodiment 6

In the above embodiments, region segmentation of the interior of the object and sound velocity determination are carried out every time that a measurement is conducted. However, in the case of multiple measurements performed on a same subject at time intervals, for instance in the case of follow-up of a drug therapy or the like, previous region segmentation information and previous sound velocities can be used in a second and subsequent measurements.

Specifically, deformation/alignment is carried out between a previous object shape and a current object shape, and regions are set so as to correspond to previous segmented regions. In the case of a breast as the object, for instance a nipple can be used as a feature point used for alignment. In case of possible enlargement of a tumor region due to disease progression, deformation/alignment may be performed for fat/mammary glands alone, while a tumor region is determined by using the methods in the embodiments above. In the present embodiment processing time can be shortened through the use of previous region segmentation information and previous sound velocities.

The apparatus may acquire general region information about the interior of the object, such as a human body atlas, and may perform region segmentation through deformation/alignment between the actual subject and the human body atlas. In that case statistical values may be used as sound velocity at each segmented region.

Embodiment 7

The bowl-shaped probe 160 is used in Embodiment 1. In the present embodiment there is used a probe suitable for generation of transmitted ultrasonic waves, for instance a cylindrical probe or an annular probe. The elements in a cylindrical probe or an annular probe generate ultrasonic waves and receive ultrasonic waves having passed through an object, as a result of which it becomes possible to generate a transmission ultrasonic image of the interior of the object. The structure of the interior of the object can be acquired with good precision on the basis of the transmission ultrasonic image, which therefore allows for good region segmentation.

As described above, the present invention relates to an information acquisition apparatus and information acquisition method for acquiring information about the interior of the object, by exploiting the photoacoustic effect. The various embodiments of the present invention relate to an apparatus or method for calculating, with good visibility, a spatial distribution of a light-absorbing body, such as blood in blood vessels in the interior of the object, that absorbs pulsed light having been irradiated thereonto.

Other Embodiments

The present invention can be realized also by a computer (or device such as CPU or MPU) of a system or device for implementing the functions of the above-described embodiments, through reading and execution of a program recorded on a storage device. The present invention can for instance be realized also by a method having steps executed by a computer of a system or device for implementing the functions of the above-described embodiments, through reading and execution of a program recorded on a storage device. The invention can also be realized by a circuit for implementing one or more functions (for instance an ASIC). To that end, the program is furnished to the computer for instance via a network or from various types of recording medium (i.e. computer-readable recording media that hold data non-transitorily) that can constitute the above storage device. Therefore, the above computer (including a device such as a CPU or an MPU), program (including a program code and a program product), and computer-readable recording medium that holds non-transitorily the above program are all encompassed within the scope of the present invention.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

The present invention makes it possible to acquire, with good precision, information pertaining to a sound velocity distribution of the interior of an object.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. An information acquisition apparatus which acquires characteristic information about an object comprising:
   a conversion unit configured to convert acoustic waves received from the object into a photoacoustic reception signal, the object comprising living tissue;
   a memory storing a program and one or more processors which, by executing the program, function as:
      a region acquisition unit configured to acquire information indicating a plurality of regions in the object, wherein the plurality of regions are set in accordance with a distance from the conversion unit;
      a distance determination unit configured to determine distances between each of the plurality of regions and the conversion unit including a first distance between a first region and the conversion unit, a second distance between a second region and the conversion unit, and a third distance between a third region and the conversion unit;
      a sound velocity determination unit configured to determine sound velocity in the plurality of regions in ascending order of distance from the conversion unit; and
      a characteristic information acquisition unit configured to acquire the characteristic information about the object, using the sound velocity in the plurality of regions and the photoacoustic reception signal,
   wherein the sound velocity determination unit determines a first sound velocity in the first region separated from the conversion unit by the first distance and being closest to the conversion unit among the plurality of regions,
   wherein the sound velocity determination unit determines a second sound velocity in the second region separated from the conversion unit by the second distance and being second closest to the conversion unit among the plurality of regions, using the first sound velocity in the first region,
   wherein the sound velocity determination unit determines a third sound velocity in the third region separated from the conversion unit by the third distance and being third closest to the conversion unit among the plurality of regions, using the second sound velocity in the second region, and
   wherein the first distance, the second distance and the third distance are determined by the distance determining unit before the sound velocity determination unit determines the first sound velocity, the second sound velocity and the third sound velocity.

2. The information acquisition apparatus according to claim 1, wherein the region acquisition unit is configured to set the plurality of regions corresponding to a plurality of mutually different tissues of the object.

3. The information acquisition apparatus according to claim 2, wherein the region acquisition unit is configured to set the plurality of regions so as to correspond to tissue of at least one of fat, a mammary gland and a tumor in the object.

4. The information acquisition apparatus according to claim 1, wherein the sound velocity determination unit is configured to determine an initial value in order to use the sound velocity in the plurality of regions in accordance with the distance from the conversion unit.

5. A signal processing method for acquiring characteristic information about an object, the method comprising:
- a conversion step of converting acoustic waves received from the object into a photoacoustic reception signal, the object comprising living tissue;
- a region acquisition step of acquiring information indicating a plurality of regions in the object, wherein the plurality of regions are set in accordance with a distance from the conversion unit;
- a distance determining step of determining distances between each of the plurality of regions and the conversion unit including a first distance between a first region and the conversion unit, a second distance between a second region and the conversion unit, and a third distance between a third region and the conversion unit;
- a sound velocity determination step of determining sound velocity in the plurality of regions in ascending order of distance from the conversion unit; and
- a characteristic information acquisition step of acquiring the characteristic information about the object, using the sound velocity in the plurality of regions and the photoacoustic reception signal,
- wherein, in the sound velocity determination step, a first sound velocity in the first region separated from the conversion unit by the first distance and being closest to the conversion unit among the plurality of regions is determined,
- wherein, in the sound velocity determination step, a second sound velocity in the second region separated from the conversion unit by the second distance and being second closest to the conversion unit among the plurality of regions is determined using the first sound velocity in the first region,
- wherein, in the sound velocity determination step, a third sound velocity in the third region separated from the conversion unit by the third distance and being third closest to the conversion unit among the plurality of regions is determined using the second sound velocity in the second region, and
- wherein the first distance, the second distance and the third distance are determined in the distance determining step before the sound velocity determination step determines the first sound velocity, the second sound velocity and the third sound velocity.

6. A non-transitory storage medium storing a program that causes a computer to execute a signal processing method for acquiring characteristic information about an object, the method comprising:
- a controlling step of controlling a conversion unit to convert acoustic waves received from the object into a photoacoustic reception signal, the object comprising living tissue;
- a region acquisition step of acquiring information indicating a plurality of regions in the object, wherein the plurality of regions are set in accordance with a distance from the conversion unit;
- a distance determining step of determining distances between each of the plurality of regions and the conversion unit including a first distance between a first region and the conversion unit, a second distance between a second region and the conversion unit, and a third distance between a third region and the conversion unit;
- a sound velocity determination step of determining sound velocity in the plurality of regions in ascending order of distance from the conversion unit; and
- a characteristic information acquisition step of acquiring the characteristic information about the object, using the sound velocity in the plurality of regions, and the photoacoustic reception signal,
- wherein, in the sound velocity determination step, a first sound velocity in the first region separated from the conversion unit by the first distance and being the closest to the conversion unit among the plurality of regions is determined,
- wherein, in the sound velocity determination step, a second sound velocity in the second region separated from the conversion unit by the second distance and being the second closest to the conversion unit among the plurality of regions is determined using the first sound velocity in the first region,
- wherein, in the sound velocity determination step, a third sound velocity in the third region separated from the conversion unit by the third distance and being the third closest to the conversion unit among the plurality of regions is determined using the second sound velocity in the second region, and
- wherein the first distance, the second distance and the third distance are determined in the distance determining step before the sound velocity determination step determines the first sound velocity, the second sound velocity and the third sound velocity.

* * * * *